United States Patent
Orser et al.

(10) Patent No.: US 9,638,702 B2
(45) Date of Patent: *May 2, 2017

(54) DETECTION OF CONFORMATIONALLY ALTERED PROTEINS

(71) Applicant: SYSTEM OF SYSTEMS ANALYTICS, INC., Fairfax, VA (US)

(72) Inventors: Cindy Orser, Lafayette, CO (US); Anne Grosset, La Croix-de-Rozon (CH); Eugene A. Davidson, Washington, DC (US)

(73) Assignee: SYSTEM OF SYSTEMS ANALYTICS, INC., Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/484,683

(22) Filed: Sep. 12, 2014

(65) Prior Publication Data

US 2015/0233948 A1    Aug. 20, 2015

Related U.S. Application Data

(63) Continuation of application No. 11/979,226, filed on Oct. 31, 2007, now abandoned, which is a continuation of application No. 10/728,246, filed on Dec. 4, 2003, now abandoned, which is a continuation-in-part of application No. 10/161,061, filed on May 30, 2002, now Pat. No. 7,166,471, said application No. 11/979,226 is a continuation-in-part of application No. 10/494,906, filed as application No. PCT/US02/17212 on May 30, 2002, now Pat. No. 7,691,639.

(Continued)

(51) Int. Cl.
*G01N 33/68* (2006.01)
*G01N 33/58* (2006.01)

(52) U.S. Cl.
CPC ....... *G01N 33/6896* (2013.01); *G01N 33/582* (2013.01)

(58) Field of Classification Search
None
See application file for complete search history.

(56) References Cited

U.S. PATENT DOCUMENTS 4,444,879 A    4/1984 Foster et al.
5,565,186 A    10/1996 Prusiner et al.
(Continued)

FOREIGN PATENT DOCUMENTS

CA    2 443 929 A1    10/2002
JP    2004-155688 A    6/2004
(Continued)

OTHER PUBLICATIONS

Buschmann et al., "Detection of cattle-derived BSE prions using transgenic mice overexpressing bovine PrPC", *Archives of Virology*, Supplement 16, pp. 75-86 (2000).

(Continued)

*Primary Examiner* — Adam M Weidner
(74) *Attorney, Agent, or Firm* — Foley & Lardner LLP

(57) ABSTRACT

The invention provides methods and kits for detecting conformationally altered proteins and prions in a sample. In one embodiment, the conformationally altered proteins and prions are associated with amyloidogenic diseases.

12 Claims, 19 Drawing Sheets

TSE Detection Schema

β-sheet
Toxic conformation disaggregated

α-helix
Non-toxic conformation

Receptor: Labeled Peptide fragment
Signal: Aggregates Light scattering Fluorescence CD
Catalytic propagation
NO signal

Related U.S. Application Data

(60) Provisional application No. 60/295,456, filed on May 31, 2001.

(56) References Cited

U.S. PATENT DOCUMENTS

| | | | |
|---|---|---|---|
| 5,721,106 | A | 2/1998 | Maggio et al. |
| 5,750,361 | A | 5/1998 | Prusiner et al. |
| 5,773,572 | A | 6/1998 | Fishleigh et al. |
| 5,891,641 | A | 4/1999 | Prusiner et al. |
| 5,955,343 | A | 9/1999 | Holmes et al. |
| 5,968,963 | A | 10/1999 | Homan |
| 5,977,324 | A | 11/1999 | Prusiner et al. |
| 6,166,187 | A | 12/2000 | Prusiner et al. |
| 6,214,565 | B1 | 4/2001 | Prusiner et al. |
| 6,290,954 | B1 | 9/2001 | Prusiner et al. |
| 6,399,314 | B1 | 6/2002 | Krishnamurthy |
| 6,451,541 | B1 | 9/2002 | Winnacker et al. |
| 6,498,017 | B2 | 12/2002 | Reisner et al. |
| 6,534,036 | B1 | 3/2003 | Collinge et al. |
| 6,600,017 | B1 * | 7/2003 | Glabe et al. .......... 530/345 |
| 6,677,125 | B2 | 1/2004 | Prusiner et al. |
| 6,750,025 | B1 | 6/2004 | Hammond et al. |
| 6,821,504 | B2 | 11/2004 | Wisniewski et al. |
| 6,849,714 | B1 | 2/2005 | Bridon et al. |
| 7,125,838 | B1 | 10/2006 | Stott |
| 7,166,471 | B2 | 1/2007 | Orser et al. |
| 7,303,907 | B2 | 12/2007 | Raven et al. |
| 7,351,526 | B2 | 4/2008 | Soto et al. |
| 7,439,041 | B2 | 10/2008 | Michelitsch et al. |
| 7,691,639 | B2 | 4/2010 | Orser et al. |
| 8,062,895 | B2 | 11/2011 | Orser et al. |
| 8,372,593 | B2 | 2/2013 | Orser et al. |
| 8,673,579 | B2 | 3/2014 | Orser et al. |
| 2001/0001061 | A1 | 5/2001 | Prusiner et al. |
| 2002/0137112 | A1 | 9/2002 | Chojkier et al. |
| 2003/0215880 | A1 | 11/2003 | Burton et al. |
| 2004/0052928 | A1 | 3/2004 | Gazit |
| 2004/0072236 | A1 | 4/2004 | Cashman et al. |
| 2004/0224365 | A1 | 11/2004 | Glabe et al. |
| 2004/0229280 | A1 | 11/2004 | Hammond et al. |
| 2005/0026165 | A1 | 2/2005 | Orser et al. |
| 2005/0112607 | A1 | 5/2005 | Bamdad et al. |
| 2005/0118645 | A1 | 6/2005 | Michelitsch et al. |
| 2005/0181998 | A1 | 8/2005 | Adessi et al. |
| 2005/0221404 | A1 | 10/2005 | Lane et al. |
| 2006/0035242 | A1 | 2/2006 | Michelitsch et al. |
| 2006/0057636 | A1 | 3/2006 | Heegaard et al. |
| 2006/0057671 | A1 | 3/2006 | Orser et al. |
| 2006/0078892 | A1 | 4/2006 | Hammond et al. |
| 2006/0178302 | A1 | 8/2006 | Krafft et al. |
| 2006/0235199 | A1 | 10/2006 | Mihara et al. |
| 2006/0275910 | A1 | 12/2006 | Orser et al. |
| 2007/0054322 | A1 | 3/2007 | Gabizon |
| 2008/0171341 | A1 | 7/2008 | Orser et al. |
| 2009/0238754 | A1 | 9/2009 | Wegrzyn et al. |
| 2009/0274621 | A1 | 11/2009 | Wegrzyn et al. |
| 2010/0233095 | A1 | 9/2010 | Duan et al. |
| 2013/0108549 | A1 | 5/2013 | Orser et al. |
| 2013/0274437 | A1 | 10/2013 | Duan et al. |
| 2015/0125396 | A1 | 5/2015 | Feuerstein et al. |
| 2015/0133632 | A1 | 5/2015 | Duan et al. |

FOREIGN PATENT DOCUMENTS

| | | |
|---|---|---|
| WO | WO 99/41279 A | 8/1999 |
| WO | WO 00/43791 A2 | 7/2000 |
| WO | WO 00/69900 A2 | 11/2000 |
| WO | WO 01/07473 A1 | 2/2001 |
| WO | WO 01/07479 | 2/2001 |
| WO | WO 01/14412 A1 | 3/2001 |
| WO | WO 01/50134 A2 | 7/2001 |
| WO | WO 01/77687 A2 | 10/2001 |
| WO | WO 02/04604 A2 | 1/2002 |
| WO | WO 02/04954 | 1/2002 |
| WO | WO 03/001881 A2 | 1/2003 |
| WO | WO 2005/016127 | 2/2005 |
| WO | WO 2006/088823 A2 | 8/2006 |

OTHER PUBLICATIONS

Chiti, F., et al., "Designing conditions for in vitro formation of amyloid protofilaments and fibrils", *Proc. Natl. Acad. Sci. USA*, vol. 96, pp. 3590-3594 (1999).

Chitnumsub et al., "The Nucleation of Monomeric Parallel Beta-Sheet-Like Structures and Their Self-Assembly in Aqueous Solution", *Biorganic & Medicinal Chemistry*, vol. 7 (1), pp. 39-59 (1999).

Koclsko et al., "Cell-Free Formation of Protease-Resistant Prion Protein", *Nature*, 370:471-474 (2004).

Lu et al., "Structural Determinants for Ligand-Receptor Conformational Selection in a Peptide G Protein-coupled Receptor", *The Journal of Biological Chemistry*, 282:17921-17929 (2007).

Maxson et al.., "A solid-phase assay for identification of modulators of prion protein interactions", *Analytical Biochemistry*, 323(1): 54-64 (2003).

Nguyen, J., et al., "Prion Protein Peptides Induce -Helix to -Sheet Conformational Transitions", *Biochemistry*, vol. 34, pp. 4186-4192 (1995).

Nicotera, P. "A Route for Prion Neuroinvasion," 31:345-348 (2001).

Pan, et al., "Conversion of alpha-helices into beta-sheets features in the formation of the scrapie prion proteins", *Proc. of National Academy of Science*, vol. 90, pp. 10962-10966 (1993).

Perutz, M.F., "Glutamine repeats and neurodegenerative disease: molecular aspects", *TIBS*, vol. 24, pp. 58-63 (1999).

Pillot et al., "The 118-135 Peptide of Human Prion Protein Forms Amyloid Fibrils and Induces Liposome Function", *J. Mol. Biol.*, vol. 274, pp. 381-393 (1997).

Prior, R., et al., "Selective binding of Soluble A 1-40 and A 1-42 to a Subset of Senile Plaque", *Am. J. Pathology*, vol. 148(6), pp. 1749-1756 (1996).

Prusiner, S.B., et al., "Prion Protein Biology", *Cell* 93:337-348 (1998).

Salmona, M., et al., "Molecular determinants of the physicochemical properties of a critical prion protein region comprising residues 106-126", *Biochemical Journal* 342:207-214 (1999).

Speed, M.A,, et al., "Specific aggregation of partially folded polypeptide chains: The molecular basis of inclusion body composition", *Nature Biotechnology* 14:1283-1287 (1996).

Speed, M.A., et al., "Polymerization Mechanism of Polypeptide Chain Aggregation", *Biotechnology and Bioengineering* 54(4):333-343 (1997).

Office Action dated Apr. 5, 2007, issued by the Examiner in U.S. Appl. No. 10/728,246 (8 pgs.).

Office Action dated Dec. 14, 2007, issued by the Examiner in U.S. Appl. No. 10/728,246 (7 pgs.).

Office Action dated Jul. 3, 2008, issued by the Examiner in U.S. Appl. No. 10/494,906 (12 pgs.).

Office Action dated Jan. 9, 2009, issued by the Examiner in U.S. Appl. No. 10/494,906 (8 pgs.).

Office Action dated Dec. 21, 2007, issued by the Examiner in U.S. Appl. No. 11/030,300 (9 pgs.).

Final Office Action dated Oct. 14, 2008, issued by the Examiner in U.S. Appl. No 11/030,300 (11 pgs.).

Office Action dated Mar. 18, 2009, issued by the Examiner in U.S. Appl. No 11/030,300 (9 pgs.).

Office Action dated Aug. 31, 2007, issued by the Examiner in U.S. Appl. No. 10/728,246 (8 pgs/).

Office Action dated Jan. 10, 2007, issued by the Examine in U.S. Appl. No. 10/728,246 (6 pgs.).

Office Action dated Sep. 8, 2004, issued by the Examiner in U.S. Appl. No. 10/161,061, now U.S. Pat. No. 7,166,471 (5 pgs.).

Office Action dated Feb. 23, 2005, issued by the Examiner in U.S. Appl. No. 10/161,061, now U.S. Pat. No. 7,166,471 (7 pgs.).

Office Action dated Jun. 15, 2005, issued by the Examiner in U.S. Appl. No. 10/161,061, now U.S. Pat. No. 7,166,471 (5 pgs.).

(56) References Cited

OTHER PUBLICATIONS

Office Action dated Sep. 27, 2005, issued by the Examiner in U.S. Appl. No. 10/161,061, now U.S. Pat. No. 7,166,471 (8 pgs.).
Office Action dated Jan. 17, 2006, issued by the Examiner in U.S. Appl. No. 10/161,061, now U.S. Pat. No. 7,166,471 (8 pgs.).
Office Action dated Apr. 13, 2007, issued by the Examiner in U.S. Appl. No. 11/030,300 (14 pgs.).
Hachiya et al., Biochemical and Biophysical Research Communications, 323:339-344 (2004), © Elsevier, Inc.
Tcherkasskaya et al. J. of Biomolecular Structure & Dynamics 21(3):353-365 (2003) © Adenine Press.
Grosset et al: "Rapid presymptomatic detection fo PrP<Sc> via conformationally responsive palindromic PrP peptides" Peptides, Elsevier, Amsterdam, US, vol. 26, No. 11, Nov. 2005(Nov. 2005), pp. 2193-2200, XP005137424 ISSN: 0196-9781.
Fraser P E et al: "Conformation and fibrillogenesis of Alzheimer A-beta peptides with selected substitution of charged residues" Journal of Molecular Biology, London, GB, vol. 244, No. 1, 1994, pp. 64-73, XP002957211 ISSN:0022-2836.
Notice of Allowance issued on Jul. 21, 2011 by the Examiner in U.S. Appl. No. 12/726,941 (US 2010/0267151).
Office Action issued on Apr. 4, 2011 by the Examiner in U.S. Appl. No. 12/726,941 (US 2010/0267151).
Office Action issued on Sep. 19, 2011 by the Examiner in U.S. Appl. No. 11/979,226 (US 2008/0171341).
Office Action issued on Apr. 12, 2011 by the Examiner in U.S. Appl. No. 11/979,226 (US 2008/0171341).
Office Action issued on Sep. 13, 2011 by the Examiner in U.S. Appl. No. 11/828,953 (US 2008/0095706).
Notice of Allowance issued on Apr. 6, 2011 by the Examiner in U.S. Appl. No. 11/828,952 (US 2008/0095706).
European Search Report issued on Mar. 17, 2011 in application No. EP 10188900.
Extended European Search Report issued on Jul. 4, 2011 in application No. EP 10188900.
Martin, "Molecular Basis of the Neurodegenerative Disorders," *The New England Journal of Medicine*, Epstein, ed., vol. 340, No. 25, pp. 1970-1980, Jun. 24, 1999.
Soto, Protein misfolding and disease: protein refolding and therapy, *FEBS Letters*, vol. 498, pp. 204-207, 2001.
Dobson, C.M., "Protein misfolding, evolution and disease", *TIBS*, vol. 24, pp. 329-332, 1999.
Dobson, C.M., "The structural basis of protein folding and its links with human disease", *Phil. Trans. R. Soc. London B*, vol. 356, pp. 133-145, 2001.
Booth, D.R., et al., "Instability, unfolding and aggregation of human lysozyme variants underlying amyloid fibrillogenesis", *Nature*, vol. 385, pp. 787-793, 1997.
Caughey et al., "Interactions and Conversions of Prion Protein Isoforms," *Protein Science*, pp. 139-169, Jan. 2001.
Office Action issued on Aug. 16, 2010 by the Examiner in U.S. Appl. No. 11/030,200 (US 2006/0057671).
Office Action issued on Jul. 29, 2010 by the Examiner in U.S. Appl. No. 12/726,941 (US 2010/0267151).
International Search Report issued on Sep. 18, 2003 in application No. PCT/US02/17212 (corresponding to US 2006/0286672).
International Search Report issued on Sep. 27, 2006 in application No. PCT/US04/40309 (corresponding to US 2005/0026165).
Notice of Allowance issued on Oct. 26, 2009 by the Examiner in U.S. Appl. No. 10/494,906 (US 2006/0286672).
Office Action issued on Jun. 11, 2009 by the Examiner in U.S. Appl. No. 10/494,906 (US 2006/0286672).
Office Action issued on Jan. 14, 2008 by the Examiner in U.S. Appl. No. 10/494,906 (US 2006/0286672).
Office Action issued on Nov. 16, 2009 by the Examiner in U.S. Appl. No. 11/030,300 (US 2006/0057671).
Office Action issued on Nov. 20, 2006 by the Examiner in U.S. Appl. No. 11/030,300 (US 2006/0057671).
Office Action issued on Sep. 16, 2009 by the Examiner in U.S. Appl. No. 11/504,692 (US 2006/0275910).
Office Action issued on Aug. 7, 2009 by the Examiner in U.S. Appl. No. 11/504,692 (US 2006/0275910).
Office Action issued on Jan. 13, 2009 by the Examiner in U.S. Appl. No. 11/504,692 (US 2006/0275910).
Office Action issued on Feb. 19, 2010 by the Examiner in U.S. Appl. No. 11/828,953 (US 2008/0095706).
Office Action issued on Oct. 1, 2009 by the Examiner in U.S. Appl. No. 11/828,953 (US 2008/0095706).
Tjernberg et al., "Assembling amyloid fibrils from designed structures containing a significant amyloid β-peptide fragment," *Biochem. J.*, vol. 366, pp. 343-351, 2002.
Usui et al., "Peptide arrays with Designed Secondary Structures for Protein Characterization Using Fluorescent Fingerprint Patterns," *Biopolymers (Peptide Science)*, vol. 76, pp. 129-139, 2004.
Wilson et al., "Conformational Transitions in Model Silk Peptides," *Biophysical Journal*, vol. 78, pp. 2690-2701, May 2000.
Vanderstichele et al., "Standardization of measurement of beta-amyloid (1-42) in crebospinal fluid and plasma," Amyloid, vol. 7, vol. 4, pp. 245-258, 2000.
Office Action issued on Dec. 16, 2009 in U.S. Appl. No. 11/979,226 (2008/0171341).
Office Action issued on Aug. 5, 2010 in U.S. Appl. No. 11/979,226 (2008/0171341).
Office Action issued on Apr. 12, 2011 in U.S. Appl. No. 11/979,226 (2008/0171341).
Office Action issued on Sep. 19, 2011 in U.S. Appl. No. 11/979,226 (2008/0171341).
Office Action issued on Mar. 12, 2014 in U.S. Appl. No. 11/979,226 (2008/0171341).
Esparza et al., "Amyloid-beta Oligomerization in Alzheimer Dementia vs. High Pathology Controls," Ann. Neurol., vol. 73, No. 1, pp. 104-119, Jan. 2013.
Johnson-Wood et al., "Amyloid precursor protein processing and $A\beta_{42}$ deposition in a transgenic mouse model of Alzheimer disease," Proc. Natl. Acad. Sci. USA, vol. 94, pp. 1550-1555, Feb. 1997.
Sergeant et al., "Truncated beta-amyloid peptide species in pre-clinical Alzheimer's disease as new targets fro the vaccination approach," Journal of Neurochemistry, vol. 85, pp. 1581-1591, Jun. 2003.
Innogenetics GMBH, "Innotest® β-/Amyloid$_{(1-42)}$," Product Information Sheet, Aug. 2010.

\* cited by examiner

Figure 2

Experiments with fluorescent probes for detection.
The data are from previous FRET experiments for proximal and distal locations in an α-helical bundle structure undergoing conformational change.

The spectra shown are for pyrene excimer formation at 480 nm, but other probes (FITC, etc.) can be used.

The driving force must be commensurate with the energetic difference between the two conformational states The process is driven by a differential interaction of the target peptide E, with the two conformations of the test PrP molecule.

Figure 10. Palindromic 33mer peptide probe.
A. Linear sequence of 33mer, 19mer and 14mer with palindromic sequences underlined and murine substituted V's and L's replace human/hamster sequence M's
B. Folded sequence demonstrating parallel palindrome and diagram showing pyrene molecules present on both ends of the peptide forming an excimer structure.

```
                        SEQUENCE LISTING

<160> NUMBER OF SEQ ID NOS: 61

<210> SEQ ID NO 1
<211> LENGTH: 33
<212> TYPE: PRT
<213> ORGANISM: Homo sapiens

<400> SEQUENCE: 1

Val Val Ala Gly Ala Ala Ala Ala Gly Ala Met His Lys Met Asn Thr
1               5                   10                  15

Lys Pro Lys Met Lys His Met Ala Gly Ala Ala Ala Ala Gly Ala Val
            20                  25                  30

Val

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Pro Lys Thr Asn Leu Lys His Val Ala Gly Ala Ala Ala Ala Gly
1               5                   10                  15

Ala Val Val

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Lys His Val Ala Gly Ala Ala Ala Ala Gly Ala Val Val
1               5                   10

<210> SEQ ID NO 4
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
            35                  40

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Val His His Gln Lys Leu Val Phe Phe Ala Glu Asp Val Gly Ser
1               5                   10                  15

Asn Lys Gly Ala Ile Ile Gly Leu
            20

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Val Arg His Gln Lys Leu Val Phe Phe Ala Glu Asp Val Gly Ser
1               5                   10                  15

Asn Lys Gly Ala Ile Ile Gly Leu
            20

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ser Asn Lys Gly Ala Ile Ile Gly Leu Met
1               5                   10

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys
            20                  25

<210> SEQ ID NO 9

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Gln Gln Gln Gln Gln Gln Gln Gln Gln Gln Gln Gln Gln Gln
1               5                   10                  15

Gln Gln Gln Gln Gln Gln Gln
            20

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Pro Lys Thr Asn Leu Lys His Val Ala Gly Ala Ala Ala Ala Gly
1               5                   10                  15

Ala Val Val

<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
            20                  25                  30

Arg Lys Cys Asn Thr Ala
        35

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Ala Glu Ser His Leu Leu Gln Trp Leu Leu Leu Leu Leu Pro Thr
1               5                   10                  15

Leu Cys Gly Pro Gly Thr Ala Ala Trp
            20                  25

<210> SEQ ID NO 13
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Trp Gly Gln Pro His Gly Gly Gly
65                  70                  75                  80

Trp Gly Gln Pro His Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
        130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
            245                 250

<210> SEQ ID NO 14
<211> LENGTH: 254
<212> TYPE: PRT
<213> ORGANISM: Mus sp.

<400> SEQUENCE: 14

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Trp Gly Gln Gly Gly Gly Thr His Asn
                85                  90                  95

Gln Trp Asn Lys Pro Ser Lys Pro Lys Thr Asn Leu Lys His Val Ala
            100                 105                 110

Gly Ala Ala Ala Ala Gly Ala Val Val Gly Gly Leu Gly Gly Tyr Met
            115                 120                 125

Leu Gly Ser Ala Met Ser Arg Pro Met Ile His Phe Gly Asn Asp Trp
            130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
            195                 200                 205

Val Glu Gln Met Cys Val Thr Gln Tyr Gln Lys Glu Ser Gln Ala Tyr
            210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 15
<211> LENGTH: 782
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ala Pro His Arg Pro Ala Pro Ala Leu Leu Cys Ala Leu Ser Leu
 1               5                  10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
        35                  40                  45

Pro Asn Ser Met Val Val Glu His Pro Glu Phe Leu Lys Ala Gly Lys
    50                  55                  60

Glu Pro Gly Leu Gln Ile Trp Arg Val Glu Lys Phe Asp Leu Val Pro
65                  70                  75                  80

Val Pro Thr Asn Leu Tyr Gly Asp Phe Phe Thr Gly Asp Ala Tyr Val
                85                  90                  95

Ile Leu Lys Thr Val Gln Leu Arg Asn Gly Asn Leu Gln Tyr Asp Leu
            100                 105                 110

His Tyr Trp Leu Gly Asn Glu Cys Ser Gln Asp Glu Ser Gly Ala Ala
        115                 120                 125

Ala Ile Phe Thr Val Gln Leu Asp Asp Tyr Leu Asn Gly Arg Ala Val
    130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Gly Val Ala Ser Gly Phe
                165                 170                 175

Lys His Val Val Pro Asn Glu Val Val Val Gln Arg Leu Phe Gln Val
            180                 185                 190

Lys Gly Arg Arg Val Val Arg Ala Thr Glu Val Pro Val Ser Trp Glu
        195                 200                 205

Ser Phe Asn Asn Gly Asp Cys Phe Ile Leu Asp Leu Gly Asn Asn Ile
    210                 215                 220

His Gln Trp Cys Gly Ser Asn Ser Asn Arg Tyr Glu Arg Leu Lys Ala

```
                    225                 230                 235                 240
Thr Gln Val Ser Lys Gly Ile Arg Asp Asn Glu Arg Ser Gly Arg Ala
                        245                 250                 255

Arg Val His Val Ser Glu Glu Gly Thr Glu Pro Glu Ala Met Leu Gln
                260                 265                 270

Val Leu Gly Pro Lys Pro Ala Leu Pro Ala Gly Thr Glu Asp Thr Ala
            275                 280                 285

Lys Glu Asp Ala Ala Asn Arg Lys Leu Ala Lys Leu Tyr Lys Val Ser
        290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
                    340                 345                 350

Glu Glu Arg Lys Ala Ala Leu Lys Thr Ala Ser Asp Phe Ile Thr Lys
                355                 360                 365

Met Asp Tyr Pro Lys Gln Thr Gln Val Ser Val Leu Pro Glu Gly Gly
    370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
                    405                 410                 415

Val Glu Arg Val Pro Phe Asp Ala Ala Thr Leu His Thr Ser Thr Ala
                420                 425                 430

Met Ala Ala Gln His Gly Met Asp Asp Gly Thr Gly Gln Lys Gln
                435                 440                 445

Ile Trp Arg Ile Glu Gly Ser Asn Lys Val Pro Val Asp Pro Ala Thr
    450                 455                 460

Tyr Gly Gln Phe Tyr Gly Gly Asp Ser Tyr Ile Ile Leu Tyr Asn Tyr
465                 470                 475                 480

Arg His Gly Gly Arg Gln Gly Gln Ile Ile Tyr Asn Trp Gln Gly Ala
                    485                 490                 495

Gln Ser Thr Gln Asp Glu Val Ala Ala Ser Ala Ile Leu Thr Ala Gln
                500                 505                 510

Leu Asp Glu Glu Leu Gly Gly Thr Pro Val Gln Ser Arg Val Val Gln
            515                 520                 525

Gly Lys Glu Pro Ala His Leu Met Ser Leu Phe Gly Gly Lys Pro Met
        530                 535                 540

Ile Ile Tyr Lys Gly Gly Thr Ser Arg Glu Gly Gly Gln Thr Ala Pro
545                 550                 555                 560

Ala Ser Thr Arg Leu Phe Gln Val Arg Ala Asn Ser Ala Gly Ala Thr
                565                 570                 575

Arg Ala Val Glu Val Leu Pro Lys Ala Gly Ala Leu Asn Ser Asn Asp
            580                 585                 590

Ala Phe Val Leu Lys Thr Pro Ser Ala Ala Tyr Leu Trp Val Gly Thr
        595                 600                 605

Gly Ala Ser Glu Ala Glu Lys Thr Gly Ala Gln Glu Leu Leu Arg Val
    610                 615                 620

Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
                    645                 650                 655
```

```
Leu Lys Asp Lys Lys Met Asp Ala His Pro Pro Arg Leu Phe Ala Cys
            660                 665                 670

Ser Asn Lys Ile Gly Arg Phe Val Ile Glu Glu Val Pro Gly Glu Leu
            675                 680                 685

Met Gln Glu Asp Leu Ala Thr Asp Val Met Leu Leu Asp Thr Trp
    690                 695                 700

Asp Gln Val Phe Val Trp Val Gly Lys Asp Ser Gln Glu Glu Glu Lys
705                 710                 715                 720

Thr Glu Ala Leu Thr Ser Ala Lys Arg Tyr Ile Glu Thr Asp Pro Ala
            725                 730                 735

Asn Arg Asp Arg Arg Thr Pro Ile Thr Val Val Lys Gln Gly Phe Glu
            740                 745                 750

Pro Pro Ser Phe Val Gly Trp Phe Leu Gly Trp Asp Asp Tyr Trp
            755                 760                 765

Ser Val Asp Pro Leu Asp Arg Ala Met Ala Glu Leu Ala Ala
            770                 775                 780

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Glu Arg Leu Lys Ala Thr Gln Val Ser Lys Gly Ile Arg Asp Asn
1               5                   10                  15

Glu Arg Ser Gly Arg Ala Arg Val His Val Ser Glu Glu Gly Thr Glu
            20                  25                  30

Pro Glu Ala Met
        35

<210> SEQ ID NO 17
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Gly Pro Leu Arg Ala Pro Leu Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
            35                  40                  45

Val Arg Arg Ala Leu Asp Phe Ala Val Gly Glu Tyr Asn Lys Ala Ser
        50                  55                  60

Asn Asp Met Tyr His Ser Arg Ala Leu Gln Val Val Arg Ala Arg Lys
65              70                  75                  80

Gln Ile Val Ala Gly Val Asn Tyr Phe Leu Asp Val Glu Leu Gly Arg
            85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
            115                 120                 125
```

```
Ala Val Pro Trp Gln Gly Thr Met Thr Leu Ser Lys Ser Thr Cys Gln
    130                 135                 140

Asp Ala
145

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Glu Glu Val Ser Ala Asp Met Pro Pro Pro Met Asp Ala Ser
1               5                   10                  15

Val Glu Glu Glu
            20

<210> SEQ ID NO 19
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln
                20                  25                  30

Gln Gln Gln Gln Gln Gln Gln Pro Pro Pro Pro Pro Pro Pro
            35                  40                  45

Pro Pro Pro Gln Leu Pro Gln Pro Pro Pro Gln Ala Gln Pro Leu Leu
50                  55                  60

Pro Gln Pro Gln Pro Pro Pro Pro Pro Pro Pro Pro Gly Pro
65                  70                  75                  80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
            100                 105                 110

Val Ala Gln Ser Val Arg Asn Ser Pro Glu Phe Gln Lys Leu Leu Gly
        115                 120                 125

Ile Ala Met Glu Leu Phe Leu Leu Cys Ser Asp Asp Ala Glu Ser Asp
    130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
            180                 185                 190

Ala Glu Leu Ala His Leu Val Arg Pro Gln Lys Cys Arg Pro Tyr Leu
        195                 200                 205

Val Asn Leu Leu Pro Cys Leu Thr Arg Thr Ser Lys Arg Pro Glu Glu
    210                 215                 220

Ser Val Gln Glu Thr Leu Ala Ala Ala Val Pro Lys Ile Met Ala Ser
225                 230                 235                 240
```

```
Phe Gly Asn Phe Ala Asn Asp Asn Glu Ile Lys Val Leu Leu Lys Ala
                245                 250                 255

Phe Ile Ala Asn Leu Lys Ser Ser Pro Thr Ile Arg Arg Thr Ala
        260                 265                 270

Ala Gly Ser Ala Val Ser Ile Cys Gln His Ser Arg Arg Thr Gln Tyr
        275                 280                 285

Phe Tyr Ser Trp Leu Leu Asn Val Leu Leu Gly Leu Leu Val Pro Val
        290                 295                 300

Glu Asp Glu His Ser Thr Leu Leu Ile Leu Gly
305                 310                 315

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Gln Gln Gln Gln Gln Gln Gln Gln Gln Gln Gln Gln Gln
1               5                   10                  15

Gln

<210> SEQ ID NO 21
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
                20                  25                  30

Arg Lys Cys Asn Thr Ala Thr Cys Ala Thr Gln Arg Leu Ala Asn Phe
            35                  40                  45

Leu Val His Ser Ser Asn Asn Phe Gly Ala Ile Leu Ser Ser Thr Asn
        50                  55                  60

Val Gly Ser Asn Thr Tyr Gly Lys Arg Asn Ala Val Glu Val Leu Lys
65                  70                  75                  80

Arg Glu Pro Leu Asn Tyr Leu Pro Leu
                85

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Ala Asn Phe Val
1               5

<210> SEQ ID NO 23
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 23

Val Phe Asn Ala Leu Pro Pro Pro Leu Ala Asn Phe Val
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Leu Val His Ser Ser
1               5

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Ser His Val Leu Phe Pro Pro Phe Leu Val His Ser Ser
1               5                   10                  15

<210> SEQ ID NO 26
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
                20                  25                  30

Met Val Lys Val Leu Asp Ala Val Arg Gly Ser Pro Ala Ile Asn Val
            35                  40                  45

Ala Val His Val Phe Arg Lys Ala Ala Asp Asp Thr Trp Glu Pro Phe
        50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145
```

```
<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Ser Val Phe Val Leu Gly Ala Leu Pro Pro Pro Leu Ala Gly
 1               5                  10                  15

Leu Val Phe Val Ser Glu
            20

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Variable amino acid
<220> FEATURE:
<221> NAME/KEY: MOD_RES
<222> LOCATION: (25)
<223> OTHER INFORMATION: Variable amino acid

<400> SEQUENCE: 28

Val Ala Ala Ala Lys Leu Arg Xaa Val Val Thr Ser Arg Gln Pro Pro
 1               5                  10                  15

Pro Pro Gln Arg Ser Thr Val Val Xaa Arg Leu Lys Ala Ala Ala Val
            20                  25                  30

<210> SEQ ID NO 29
<211> LENGTH: 33
<212> TYPE: PRT
<213> ORGANISM: Mus sp.

<400> SEQUENCE: 29

Val Val Ala Gly Ala Ala Ala Ala Gly Ala Val His Lys Leu Asn Thr
 1               5                  10                  15

Lys Pro Lys Leu Lys His Val Ala Gly Ala Ala Ala Gly Ala Val
            20                  25                  30

Val

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Variable amino acid

<400> SEQUENCE: 30

Gln Arg Ser Thr Val Val Xaa Arg Leu Lys Ala Ala Ala Val
 1               5                  10

<210> SEQ ID NO 31
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ala Ala Val
1

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Variable amino acid

<400> SEQUENCE: 32

Val Ala Ala Ala Lys Leu Arg Xaa Val Val Thr Ser Arg Gln
1               5                   10

<210> SEQ ID NO 33
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Val Val Ala Gly Ala Ala Ala Gly Ala Met His Lys Met Lys Pro
1               5                   10                  15

Lys Thr Asn Met Lys His Met Ala Gly Ala Ala Ala Gly Ala Val
            20                  25                  30

Val

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Val Ala Gly Ala Ala Ala Gly Ala Val His Lys Leu Asn Thr
1               5                   10                  15

Lys Pro Lys

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Val Ala Gly Ala Ala Ala Gly Ala Val His Lys Leu
1               5                   10
```

```
<210> SEQ ID NO 36
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Val Gly Gly Val Met Leu Gly Ile Ile Ala Gly Lys Asn Ser Gly
 1               5                  10                  15

Val Asp Glu Ala Phe Phe Val Leu Lys Gln His His Val Glu Tyr Gly
            20                  25                  30

Ser Asp His Arg Phe Glu Ala Asp
        35                  40

<210> SEQ ID NO 37
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Gly Ile Ile Ala Gly Lys Asn Ser Gly Val Asp Glu Ala Phe Phe
 1               5                  10                  15

Val Leu Lys Gln His His Val Glu
            20

<210> SEQ ID NO 38
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Gly Ile Ile Ala Gly Lys Asn Ser Gly Val Asp Glu Ala Phe Phe
 1               5                  10                  15

Val Leu Lys Gln His Arg Val Glu
            20

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Met Leu Gly Ile Ile Ala Gly Lys Asn Ser Gly
 1               5                  10

<210> SEQ ID NO 40
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Lys Lys Lys Lys Lys Lys Lys Lys Lys Lys Lys Lys Lys Lys Lys
```

```
                1               5                   10                  15
Lys Lys Lys Lys Lys Lys Lys Lys Lys Lys
                20                  25

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Gln Gln Gln Gln Gln Gln Gln Gln Gln Gln Gln Gln Gln Gln Gln
  1               5                   10                  15

Gln Gln Gln Gln Gln Gln Gln
                20

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Val Ala Gly Ala Ala Ala Ala Gly Ala Val His Lys Leu Asn Thr
  1               5                   10                  15

Lys Pro Lys

<210> SEQ ID NO 43
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Thr Asn Cys Lys Arg Lys Glu Val Gln His Ser Glu Ile Pro Thr
  1               5                   10                  15

Ala Lys Leu His Asn Leu Ala Val Ser Leu Val Ile Leu Phe Val Gln
                20                  25                  30

Leu Lys Leu Ile Gly Met
         35

<210> SEQ ID NO 44
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Ala Ala Thr Gly Pro Gly Cys Leu Thr Pro Leu Leu Leu Leu Leu
  1               5                   10                  15

Trp Gln Leu Leu His Ser Glu Ala Met
                20                  25

<210> SEQ ID NO 45
<211> LENGTH: 253
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 45

```
Gly Val Ile Leu Phe Ile Leu Phe Ser Ile Leu Leu Ile Val Pro Pro
  1               5                  10                  15

Ser Ser Phe Leu Val Met Ser Ser Gly Arg Gln Tyr Tyr Ala Gln Ser
             20                  25                  30

Glu Arg Glu Tyr Gln Thr Ile Cys Met Gln Glu Val Val Arg Glu Met
         35                  40                  45

Met Lys Val Asp Thr Glu Thr Phe Asn Glu Gly Lys Thr Thr Thr Thr
 50                  55                  60

Val Thr His Gln Lys Ile Thr Ile Asn Val Cys Asp His Val Phe Asn
 65                  70                  75                  80

Asn Gln Asn Ser Tyr Glu Asp Met Pro Arg Tyr Tyr Val Gln Asn Pro
                 85                  90                  95

Tyr Arg His Met Asn Glu Arg Tyr Tyr Arg Asp Glu Tyr Asp Ser Gly
            100                 105                 110

Phe His Ile Ile Pro Arg Ser Met Ala Ser Gly Leu Met Tyr Gly Gly
        115                 120                 125

Leu Gly Gly Val Val Ala Gly Ala Ala Ala Gly Ala Met His Lys
130                 135                 140

Met Asn Thr Lys Pro Lys Ser Pro Lys Asn Trp Gln Ser His Thr Gly
145                 150                 155                 160

Gly Gly Gln Gly Trp Gly Gly Gly His Pro Gln Gly Trp Gly Gly Gly
                165                 170                 175

His Pro Gln Gly Trp Gly Gly Gly His Pro Gln Gly Trp Gly Gly Gly
            180                 185                 190

His Pro Gln Gly Trp Gly Gly Gly Gln Pro Pro Tyr Arg Asn Gly
        195                 200                 205

Gly Pro Ser Gly Gln Gly Pro Tyr Arg Ser Gly Gly Thr Asn Trp Gly
    210                 215                 220

Gly Pro Lys Pro Arg Lys Lys Cys Leu Gly Leu Asp Ser Trp Thr Ala
225                 230                 235                 240

Val Phe Leu Val Leu Met Trp Cys Gly Leu Asn Ala Met
                245                 250
```

<210> SEQ ID NO 46
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Gly Val Ile Leu Phe Ile Leu Phe Ser Ile Leu Leu Ile Val Pro Pro
  1               5                  10                  15

Ser Ser Phe Leu Val Thr Ser Ser Arg Arg Gly Asp Tyr Tyr Ala
             20                  25                  30

Gln Ser Glu Lys Gln Tyr Gln Thr Val Cys Met Gln Glu Val Val Arg
         35                  40                  45

Glu Met Met Lys Val Asp Thr Glu Thr Phe Asn Glu Gly Lys Thr Thr
 50                  55                  60

Thr Thr Val Thr His Gln Lys Ile Thr Ile Asn Val Cys Asp His Val
```

```
            65                  70                  75                  80
        Phe Asn Asn Gln Asn Ser Tyr Gln Asp Val Pro Arg Tyr Tyr Val Gln
                        85                  90                  95
        Asn Pro Tyr Arg Tyr Met Asn Glu Arg Tyr Tyr Arg Asp Glu Trp Asp
                        100                 105                 110
        Asn Gly Phe His Ile Met Pro Arg Ser Met Ala Ser Gly Leu Met Tyr
                        115                 120                 125
        Gly Gly Leu Gly Gly Val Val Ala Gly Ala Ala Ala Gly Ala Val
                        130                 135                 140
        His Lys Leu Asn Thr Lys Pro Lys Ser Pro Lys Asn Trp Gln Asn His
        145                 150                 155                 160
        Thr Gly Gly Gly Gln Gly Trp Gly Gly His Pro Gln Gly Trp Ser
                        165                 170                 175
        Gly Gly His Pro Gln Gly Trp Ser Gly Gly His Pro Gln Gly Trp Gly
                        180                 185                 190
        Gly Gly His Pro Gln Gly Trp Thr Gly Gly Gln Pro Pro Tyr Arg Asn
                        195                 200                 205
        Gly Gly Pro Ser Gly Gln Gly Pro Tyr Arg Ser Gly Gly Thr Asn Trp
                        210                 215                 220
        Gly Gly Pro Lys Pro Arg Lys Lys Cys Leu Gly Val Asp Thr Trp Met
        225                 230                 235                 240
        Thr Val Phe Leu Ala Leu Leu Trp Tyr Gly Leu Asn Ala Met
                        245                 250

<210> SEQ ID NO 47
<211> LENGTH: 782
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Ala Leu Glu Ala Met Ala Arg Asp Leu Pro Asp Val Ser Trp Tyr
1               5                   10                  15
Asp Asp Asp Trp Gly Leu Phe Trp Gly Val Phe Ser Pro Pro Glu Phe
                20                  25                  30
Gly Gln Lys Val Val Thr Ile Pro Thr Arg Arg Asp Arg Asn Ala Pro
                35                  40                  45
Asp Thr Glu Ile Tyr Arg Lys Ala Ser Thr Leu Ala Glu Thr Lys Glu
            50                  55                  60
Glu Glu Gln Ser Asp Lys Gly Val Trp Val Phe Val Gln Asp Trp Thr
65                  70                  75                  80
Asp Leu Leu Met Val Asp Asp Thr Ala Leu Asp Glu Gln Met Leu Glu
                85                  90                  95
Gly Pro Val Glu Glu Ile Val Phe Arg Gly Ile Lys Asn Ser Cys Ala
                100                 105                 110
Phe Leu Arg Pro Pro His Ala Asp Met Lys Lys Asp Lys Leu Arg Pro
                115                 120                 125
Ser Thr Arg Tyr Ala Ala Lys Gly Gly Leu Ala Glu Trp Phe Gly Asp
                130                 135                 140
Pro Glu Ser Gly Glu Ala Val Gln Val Pro Gln Ala Arg Leu Val Arg
145                 150                 155                 160
Leu Leu Glu Gln Ala Gly Thr Lys Glu Ala Glu Ser Ala Gly Thr Gly
                165                 170                 175
```

-continued

```
Val Trp Leu Tyr Ala Ala Ser Pro Thr Lys Leu Val Phe Ala Asp Asn
            180                 185                 190
Ser Asn Leu Ala Gly Ala Lys Pro Leu Val Glu Val Ala Arg Thr Ala
            195                 200                 205
Gly Ala Ser Asn Ala Arg Val Gln Phe Leu Arg Thr Ser Ala Pro Ala
            210                 215                 220
Thr Gln Gly Gly Glu Arg Ser Thr Gly Gly Lys Tyr Ile Ile Met Pro
225                 230                 235                 240
Lys Gly Gly Phe Leu Ser Met Leu His Ala Pro Glu Lys Gly Gln Val
            245                 250                 255
Val Arg Ser Gln Val Pro Thr Gly Gly Leu Glu Glu Asp Leu Gln Ala
            260                 265                 270
Thr Leu Ile Ala Ser Ala Ala Val Glu Asp Gln Thr Ser Gln Ala Gly
            275                 280                 285
Gln Trp Asn Tyr Ile Ile Gln Gly Gln Arg Gly Gly His Arg Tyr Asn
            290                 295                 300
Tyr Leu Ile Ile Tyr Ser Asp Gly Gly Tyr Phe Gln Gly Tyr Thr Ala
305                 310                 315                 320
Pro Asp Val Pro Val Lys Asn Ser Gly Glu Ile Arg Trp Ile Gln Lys
            325                 330                 335
Gln Gly Thr Gly Asp Asp Asp Met Gly His Gln Ala Ala Met Ala Thr
            340                 345                 350
Ser Thr His Leu Thr Ala Ala Asp Phe Pro Val Arg Glu Val Asn Ala
            355                 360                 365
Ile His Ser Ser Leu Tyr Ser Leu Gly Leu Gly Asp Thr Gln Asp Pro
            370                 375                 380
Asp Arg Trp Asn Lys Phe Phe Gln Lys Phe Leu Pro Thr Glu Gly Gly
385                 390                 395                 400
Glu Pro Leu Val Ser Val Gln Thr Gln Lys Pro Tyr Asp Met Lys Thr
            405                 410                 415
Ile Phe Asp Ser Ala Thr Lys Leu Ala Ala Lys Arg Glu Glu Thr Asn
            420                 425                 430
Ala Gln Lys Gly Lys Trp Val Phe Ile Lys Gly Asp Lys Gly His Asp
            435                 440                 445
Leu Ile Phe Cys Asp Glu Ser Lys Leu Ala Gly Gln Ala Phe Pro Asn
450                 455                 460
Glu Asp Ala Val Leu Ser Val Ser Met Thr Gly Ala Gly Asn Ser Val
465                 470                 475                 480
Lys Tyr Leu Lys Ala Leu Lys Arg Asn Ala Ala Asp Glu Lys Ala Thr
            485                 490                 495
Asp Glu Thr Gly Ala Pro Leu Ala Pro Lys Pro Gly Leu Val Gln Leu
            500                 505                 510
Met Ala Glu Pro Glu Thr Gly Glu Glu Ser Val His Val Arg Ala Arg
            515                 520                 525
Gly Ser Arg Glu Asn Asp Arg Ile Gly Lys Ser Val Gln Thr Ala Lys
            530                 535                 540
Leu Arg Glu Tyr Arg Asn Ser Asn Ser Gly Cys Trp Gln His Ile Asn
545                 550                 555                 560
Asn Gly Leu Asp Leu Ile Phe Cys Asp Gly Asn Asn Phe Ser Glu Trp
            565                 570                 575
Ser Val Pro Val Glu Thr Ala Arg Val Val Arg Gly Lys Val Gln
            580                 585                 590
Phe Leu Arg Gln Val Val Val Glu Asn Pro Val Val His Lys Phe Gly
```

```
                595                 600                 605
Ser Ala Val Gly Gly Lys Lys Tyr Lys Leu Gly Ser Lys Phe Tyr Gly
    610                 615                 620

Leu Phe Thr Ala Ser Glu Phe Gly Gln Val Glu Arg His Gln Val Ala
625                 630                 635                 640

Arg Gly Asn Leu Tyr Asp Asp Leu Gln Val Thr Phe Ile Ala Ala Ala
                645                 650                 655

Gly Ser Glu Asp Gln Ser Cys Glu Asn Gly Leu Trp Tyr His Leu Asp
                660                 665                 670

Tyr Gln Leu Asn Gly Asn Arg Leu Gln Val Thr Lys Leu Ile Val Tyr
                675                 680                 685

Ala Asp Gly Thr Phe Phe Asp Gly Tyr Leu Asn Thr Pro Val Pro Val
690                 695                 700

Leu Asp Phe Lys Glu Val Arg Trp Ile Gln Leu Gly Pro Glu Lys Gly
705                 710                 715                 720

Ala Lys Leu Phe Glu Pro His Glu Val Val Met Ser Asn Pro Arg Ala
                725                 730                 735

Glu Pro Val Arg Gly Gln Pro Ala Gly Ala Gln Ser Ala Gly Arg Ser
                740                 745                 750

Ala Thr Ala Ala Arg Val Pro Leu Ser Leu Ala Cys Leu Ala Leu Ser
                755                 760                 765

Leu Ala Cys Leu Leu Ala Pro Ala Pro Arg His Pro Ala Met
770                 775                 780
```

<210> SEQ ID NO 48
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Met Ala Glu Pro Glu Thr Gly Glu Glu Ser Val His Val Arg Ala Arg
1               5                   10                  15

Gly Ser Arg Glu Asn Asp Arg Ile Gly Lys Ser Val Leu Thr Ala Lys
            20                  25                  30

Leu Arg Glu Tyr
        35
```

<210> SEQ ID NO 49
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Ala Asp Gln Cys Thr Ser Lys Ser Leu Thr Met Thr Gly Gln Trp Pro
1               5                   10                  15

Val Ala Tyr Ile Gln Phe Ser Cys Phe Ala Lys Arg Lys Leu His Pro
            20                  25                  30

Gln Asp His Phe Pro Cys Asn Asp Leu Asn Pro Gln Thr Lys Thr Cys
        35                  40                  45

Thr Thr Arg Gly Leu Glu Val Asp Leu Phe Tyr Asn Val Gly Ala Val
    50                  55                  60

Ile Gln Lys Arg Ala Arg Val Val Gln Leu Ala Arg Ser His Tyr Met
```

```
                65                  70                  75                  80
Asp Asn Ser Ala Lys Asn Tyr Glu Gly Val Ala Phe Asp Leu Ala Arg
                85                  90                  95

Arg Val Gly Glu Glu Val Ser Ala Asp Met Pro Gly Gly Val Leu
            100                 105                 110

Arg Pro Pro Lys Gly Pro Ser Ser Gly Ala Ala Pro Ser Val Ala Leu
            115                 120                 125

Ala Val Ala Leu Ile Ala Leu Leu Leu Leu Pro Ala Arg Leu Pro Gly
        130                 135                 140

Ala Met
145

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Glu Glu Val Ser Ala Asp Met Pro Pro Pro Met Asp Ala Ser
  1               5                  10                  15

Val Glu Glu Glu
            20

<210> SEQ ID NO 51
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Leu Ile Leu Leu Thr Ser His Glu Asp Glu Val Pro Val Leu Leu
  1               5                  10                  15

Gly Leu Leu Val Asn Leu Leu Trp Ser Tyr Phe Tyr Gln Thr Arg Arg
            20                  25                  30

Ser His Gln Cys Ile Ser Val Ala Ser Gly Ala Ala Thr Arg Arg Ile
        35                  40                  45

Thr Pro Ser Ser Ser Lys Leu Asn Ala Ile Phe Ala Lys Leu Leu Val
    50                  55                  60

Lys Ile Glu Asn Asp Asn Ala Phe Asn Gly Phe Ser Ala Met Ile Lys
65                  70                  75                  80

Pro Val Ala Ala Ala Leu Thr Glu Gln Val Ser Glu Glu Pro Arg Lys
                85                  90                  95

Ser Thr Arg Thr Leu Cys Pro Leu Leu Asn Val Leu Tyr Pro Arg Cys
            100                 105                 110

Lys Gln Pro Arg Val Leu His Ala Leu Glu Ala Phe Arg Trp Leu Ala
        115                 120                 125

Ala Arg Leu Ser Arg Pro Ala Gly Asn Lys Lys Ile Glu Lys Tyr Leu
    130                 135                 140

Glu Leu Gln Leu Arg Pro Leu Asn Ser Asp Met Leu Ala Lys Ile Val
145                 150                 155                 160

Lys Asn Leu Cys Glu Asp Ala Val Met Arg Val Asp Ser Glu Ala Asp
                165                 170                 175

Asp Ser Cys Leu Leu Phe Leu Glu Met Ala Ile Gly Leu Leu Lys Gln
```

```
            180                 185                 190
Phe Glu Pro Ser Asn Arg Val Ser Gln Ala Val Ile Asn Glu Cys Ile
        195                 200                 205

Thr Leu Cys His Asn Val Arg Asp Lys Lys Thr Ala Ser Leu Glu Lys
    210                 215                 220

Lys Pro Arg His Leu Pro Glu Glu Ala Val Ala Pro Gly Pro Pro Pro
225                 230                 235                 240

Pro Pro Pro Pro Pro Pro Gln Pro Gln Pro Leu Leu Pro Gln Ala
                245                 250                 255

Gln Pro Pro Pro Gln Pro Leu Gln Pro Pro Pro Pro Pro Pro Pro
            260                 265                 270

Pro Pro Pro Gln Gln Gln Gln Gln Gln Gln Gln Gln Gln Gln
        275                 280                 285

Gln Gln Gln Gln Gln Gln Gln Gln Gln Phe Ser Lys Leu Ser Glu
        290                 295                 300

Phe Ala Lys Met Leu Lys Glu Leu Thr Ala Met
305                 310                 315
```

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Gln Gln Gln Gln Gln Gln Gln Gln Gln Gln Gln Gln Gln Gln Gln Gln
 1               5                  10                  15

Gln
```

<210> SEQ ID NO 53
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Leu Pro Leu Tyr Asn Leu Pro Glu Arg Lys Leu Val Glu Val Ala Asn
 1               5                  10                  15

Arg Lys Gly Tyr Thr Asn Ser Gly Val Asn Thr Ser Ser Leu Ile Ala
                20                  25                  30

Gly Phe Asn Asn Ser Ser His Val Leu Phe Asn Ala Leu Arg Gln Thr
            35                  40                  45

Ala Cys Thr Ala Thr Asn Cys Lys Arg Lys Glu Val Gln His Ser Glu
    50                  55                  60

Ile Pro Thr Ala Lys Leu His Asn Leu Ala Val Ser Leu Val Ile Leu
65                  70                  75                  80

Phe Val Gln Leu Lys Leu Ile Gly Met
                85
```

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 54

Val Phe Asn Ala Leu
1               5

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Phe Asn Ala Leu Pro Pro Pro Pro Leu Ala Asn Phe Val
1               5                   10

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Ser His Val Leu Phe
1               5

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Ser His Val Leu Phe Pro Pro Pro Phe Leu Val His Ser Ser
1               5                   10                  15

<210> SEQ ID NO 58
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Lys Pro Asn Thr Val Val Ala Thr Thr Ser Tyr Ser Tyr Pro Ser
1               5                   10                  15

Leu Leu Ala Ala Ile Thr Tyr Arg Arg Pro Gly Ser Asp Asn Ala Thr
                20                  25                  30

Phe Val Val Glu Ala His Glu His Phe Pro Ser Ile Gly Leu Ala Lys
            35                  40                  45

Trp Tyr Ser Lys Thr Asp Ile Glu Val Lys Tyr Ile Gly Glu Val Phe
    50                  55                  60

Glu Glu Glu Thr Thr Leu Gly His Leu Glu Gly Ser Glu Ser Thr Lys
65                  70                  75                  80

Gly Ser Ala Phe Pro Glu Trp Thr Asp Asp Ala Ala Lys Arg Phe Val
                85                  90                  95

His Val Ala Val Asn Ile Ala Pro Ser Gly Arg Val Ala Asp Leu Val
            100                 105                 110
```

```
Lys Val Met Leu Pro Cys Lys Ser Glu Gly Thr Gly Thr Pro Gly Ala
        115                 120                 125
Glu Ser Val Phe Val Leu Gly Ala Leu Cys Leu Leu Leu Arg His
    130                 135                 140
Ser Ala Met
145

<210> SEQ ID NO 59
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Ser Val Phe Val Leu Gly Ala Leu Pro Pro Pro Leu Ala Gly
1               5                   10                  15
Leu Val Phe Val Ser Glu
            20

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Variable amino acid
<220> FEATURE:
<221> NAME/KEY: MOD_RES
<222> LOCATION: (25)
<223> OTHER INFORMATION: Variable amino acid

<400> SEQUENCE: 60

Val Ala Ala Ala Lys Leu Arg Xaa Val Val Thr Ser Arg Gln Pro Pro
1               5                   10                  15
Pro Pro Gln Arg Ser Thr Val Val Xaa Arg Leu Lys Ala Ala Ala Val
            20                  25                  30

<210> SEQ ID NO 61
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Val Val Ala Gly Ala Ala Ala Ala Gly Ala Val His Lys Leu Lys Pro
1               5                   10                  15
Lys Thr Asn Leu Lys His Val Ala Gly Ala Ala Ala Gly Ala Val
            20                  25                  30
Val
```

DETECTION OF CONFORMATIONALLY ALTERED PROTEINS

RELATED APPLICATIONS

This application is a continuation application of U.S. application Ser. No. 11/979,226, filed Oct. 31, 2007, now abandoned, which is a continuation application of U.S. application Ser. No. 10/728,246, filed Dec. 4, 2003, now abandoned, which is a continuation-in-part application of U.S. application Ser. No. 10/161,061, file May 30, 2002, which issued as U.S. Pat. No. 7,166,471, which claims priority from U.S. Provisional Patent Application 60/295,456, filed May 31, 2001.

FIELD OF THE INVENTION

The invention provides methods and kits for detecting conformationally altered proteins and prions in a sample.

In one embodiment, the conformationally altered proteins and prions are associated with amyloidogenic diseases.

BACKGROUND OF THE INVENTION

1. Conformationally Altered Proteins and Prions and Associated Diseases.

The conversion of normally soluble proteins into conformationally altered insoluble proteins is thought to be a causative process in a variety of other diseases. Structural conformational changes are required for the conversion of a normally soluble and functional protein into a defined, insoluble state. Examples of such insoluble proteins include: A. beta. peptide in amyloid plaques of Alzheimer's disease (AD) and cerebral amyloid angiopathy (CAA); .alpha.-synuclein deposits in Lewy bodies of Parkinson's disease, tau in neurofibrillary tangles in frontal temporal dementia and Pick's disease; superoxide dismutase in amylotrophic lateral sclerosis; huntingtin in Huntington's disease; and prions in Creutzfeldt-Jakob disease (CJD): (for reviews, see Glenner et al. (1989) J. Neurol. Sci. 94:1-28; Haan et al. (1990) Clin. Neurol. Neurosurg. 92(4):305-310).

Often these highly insoluble proteins form aggregates composed of nonbranching fibrils with the common characteristic of a beta.-pleated sheet conformation. In the CNS, amyloid can be present in cerebral and meningeal blood vessels (cerebrovascular deposits) and in brain parenchyma (plaques). Neuropathological studies in human and animal models indicate that cells proximal to amyloid deposits are disturbed in their normal functions (Mandybur (1989) Acta Neuropathol. 78:329-331; Kawai et al. (1993) Brain Res. 623:142-6; Martin et al. (1994) Am. J. Pathol. 145:1348-1381; Kalaria et al. (1995) Neuroreport 6:477-80; Masliah et al. (1996) J. Neurosci. 16:5795-5811). Other studies additionally indicate that amyloid fibrils may actually initiate neurodegeneration (Lendon et al. (1997) J. Am. Med. Assoc. 277:825-31; Yankner (1996) Nat. Med. 2:850-2; Selkoe (1996) J. Biol. Chem. 271:18295-8; Hardy (1997) Trends Neurosci. 20:154-9).

In both AD and CAA, the main amyloid component is the amyloid beta protein (A. beta.). The A. beta. peptide, which is generated from the amyloid beta precursor protein (APP) by the action of two putative secretases, is present at low levels in the normal CNS and blood. Two major variants, $A.beta._{1-40}$ and $A.beta._{1-42}$, are produced by alternative carboxy-terminal truncation of APP (Selkoe et al. (1988) Proc. Natl. Acad. Sci. USA 85:7341-7345; Selkoe, (1993) Trends Neurosci 16:403-409). $A.beta._{1-42}$ is the more fibrillogenic and more abundant of the two peptides in amyloid deposits of both AD and CAA. In addition to the amyloid deposits in AD cases described above, most AD cases are also associated with amyloid deposition in the vascular walls (Hardy (1997), supra; Haan et al. (1990), supra; Terry et al., supra; Vinters (1987), supra; Itoh et al. (1993), supra; Yamada et al. (1993), supra; Greenberg et al. (1993), supra; Levy et al. (1990), supra). These vascular lesions are the hallmark of CAA, which can exist in the absence of AD.

Human transthyretin (TTR) is a normal plasma protein composed of four identical, predominantly beta.-sheet structured units, and serves as a transporter of the hormone thyroxin. Abnormal self assembly of TTR into amyloid fibrils causes two forms of human diseases, namely senile systemic amyloidosis (SSA) and familial amyloid polyneuropathy (FAP) (Kelly (1996) Curr Opin Struct Biol 6(1):11-7). The cause of amyloid formation in FAP is point mutations in the TTR gene; the cause of SSA is unknown. The clinical diagnosis is established histologically by detecting deposits of amyloid in situ in biopsy material.

To date, little is known about the mechanism of TTR conversion into amyloid in vivo. However, several laboratories have demonstrated that amyloid conversion may be simulated in vitro by partial denaturation of normal human TTR [McCutchen, Colon et al. (1993) Biochemistry 32(45): 12119-27; McCutchen and Kelly (1993) Biochem Biophys Res Commun 197(2) 415-21]. The mechanism of conformational transition involves a monomeric conformational intermediate which poly_merizes into linear beta.-sheet structured amyloid fibrils [Lai, Colon et al. (1996) Biochemistry 35(20):6470-82]. The process can be mitigated by binding with stabilizing molecules such as thyroxin or triiodophenol (Miroy, Lai et al. (1996) Proc Natl Acad Sci USA 93(26):15051-6).

The precise mechanisms by which neuritic plaques are formed and the relationship of plaque formation to the disease-associated neurodegenerative processes are not well-defined. The amyloid fibrils in the brains of Alzheimer's and prion disease patients are known to result in the inflammatory activation of certain cells. For example, primary microglial cultures and the THP-1 monocytic cell line are stimulated by fibrillar .beta.-amyloid and prion peptides to activate identical tyrosine kinase-dependent inflammatory signal transduction cascades. The signaling response elicited by .beta.-amyloid and prion fibrils leads to the production of neurotoxic products, which are in part responsible for the neurodegeneration. C. K. Combs et al, J Neurosci 19:928-39 (1999).

2. Prions.

Prions are infectious pathogens that cause central nervous system spongiform encephalopathies in humans and animals. Prions are distinct from bacteria, viruses and viroids. A potential prion precursor is a protein referred to as PrP 27-30, a 28 kdalton hydrophobic glycoprotein that poly_merizes (aggregates) into rod-like filaments found as plaques in infected brains. The normal protein homologue differs from prions in that it is readily degradable, whereas prions are highly resistant to proteases. It has been suggested that prions may contain extremely small amounts of highly infectious nucleic acid, undetectable by conventional assay methods Benjamin Lewin, *Genes IV* (Oxford Univ. Press, New York, 1990 at p. 1080. The predominant hypothesis at present is that no nucleic acid component is necessary for the infectivity of prion protein.

Complete prion protein-encoding genes have since been cloned, sequenced and expressed in transgenic animals. $PrP^C$ is encoded by a single-copy host gene and is normally found at the outer surface of neurons. During a post-translational process, PrP$^{Sc}$ is formed from the normal, cellular PrP isoform (PrP$^C$), and prion diseases result from conversion of PrP$^C$ into a modified isoform called PrP$^{Sc}$. PrP$^{Sc}$ is necessary for both the transmission and pathogenesis of the transmissible neurodegenerative diseases of animals and humans.

The normal prion protein (PrP) is a cell-surface metalloglycoprotein that is mostly an alpha-helix and coiled-loop structure as shown in FIG. 8, and is usually expressed in the central nervous and lymph systems. It is believed to serve as an antioxidant and is thought to be associated with cellular homeostasis. The abnormal form of PrP, however, is a confor_mer which is resistant to proteases and is predominantly beta-sheet in its secondary structure, as shown in FIG. 9. It is believed that this conformational change in secondary structure leads to aggregation and eventual neurotoxic plaque deposition in the prion-disease process.

Prion-associated diseases include scrapie of sheep and goats, chronic wasting disease of deer and elk, and bovine spongiform encephalopathy (BSE) of cattle (Witesmith, J. and Wells, Microbiol. Immunol. 172:21-38 (1991)). Four prion diseases of humans have been identified: (1) kuru, (2) Creutzfeldt-Jakob disease (CJD), (3) Gerstmann-Strassler-Scheinker Disease (GSS), and (4) fatal familial insomnia (FFI) (Gajdusek, D. C., Science 197:943-960 (1977); Medori et al., N. Engl. J Med. 326:444-449 (1992)).

Prion diseases are transmissible and insidious. For example, the long incubation times associated with prion diseases will not reveal the full extent of iatrogenic CJD for decades in thousands of people treated with cadaver-sourced HGH worldwide. The importance of detecting prions in biological products has been heightened by the possibility that bovine prions have been transmitted to humans who developed new variant Creutzfeldt-Jakob disease (nvCJD) (G. Chazot et al., Lancet 347:1181 (1996); R. G. Will et al. Lancet 347:921-925 (1996)).

Diseases caused by prions are hard to diagnose: the disease may be latent or subclinical (abnormal prions are detectable but symptoms are not). Moreover, normal homologues of a prion-associated protein exist in the brains of uninfected organisms, further complicating detection. Ivan Roitt, et al., *Immunology* (Mosby-Year Book Europe Limited, 1993), at 15.1.

Current techniques used to detect the presence of prion-related infections rely on gross morphological changes in the brain and immunochemical techniques that are generally applied only after symptoms are manifest. Many of the current detection methods rely on antibody-based assays or affinity chromatography that use brain tissue from dead animals, and in some cases capillary immunoelectrophoresis of blood samples.

Brain-tissue-based assays can lead to late detection and require slaughtering the animal to be tested. Prionic-Check also entails slaughtering an animal to obtain a liquefied-brain tissue sample, which is subjected to an antibody using Western Blot. Although results are obtained in six to seven hours, the test does not account for the six-month lag time between PrP$^S$ accumulation in the brain and the onset of clinical symptoms. Tonsillar biopsy sampling, and blood and cerebrospinal sampling, while accurate, can require surgical intervention and take weeks to obtain results. Electrospray ionization mass spectrometry (ESI-MS), nuclear magnetic resonance NMR, circular dichroism (CD) and other non-amplified structural techniques require large amounts of sample and expensive equipment that is typically located a substantial distance from the sample source.

Detection methods for conformationally altered proteins associated with the aforementioned disorders such as Alzheimer's disease and CAA are also inadequate in that, like the previously mentioned prion detection techniques, they often require post-mortem tissue sampling, Accordingly, the need exists for reliable and affordable detection methods for conformationally altered proteins and prions. Such methods should be applicable during the life of the subject at issue in order to obtain rapid diagnoses and facilitate prophylactic or remedial treatments.

SUMMARY OF THE INVENTION

The invention provides reliable, affordable, and safe methods for the detection of conformationally altered proteins and prions associated with a variety of diseases. Methods of the invention can be applied to obtain rapid diagnoses and facilitate prophylactic or remedial treatments. Significantly, the methods of the invention use small amounts of sample and are therefore less invasive and more readily applied than known diagnostic techniques. Further, methods of the invention can be used to analyze samples from a living subject and are not limited to samples obtained post mortem; and may be utilized in a manner that ensures that infectious material is not propagated during testing.

The invention overcomes many of the problems associated with prior art diagnostic techniques by using catalytic propagation to exploit conformational changes in conformationally altered protein or prions associated with a particular disease process, such as transmissible spongiform encephalopathy (TSE). Catalytic propagation may be used to amplify the number of existing conformationally altered protein fragments or prions in a sample and causes detectable aggregates to form as follows:

Upon interaction of a sample containing conformationally altered protein or prions with a conformational probe as defined hereinafter, the probe undergoes a conformational change and adopts the conformation of, and aggregates with, the conformationally altered protein (which may be soluble or insoluble) or prions. The resulting aggregates which exhibit ββ sheet formation, may be readily detected using standard analytical techniques. As a result, the invention facilitates rapid and cost-effective analysis of small sample sizes and is widely applicable to tissues and body fluids from a variety of sources including, but not limited to, the brain.

The invention enables detection of small amounts of disease-associated conformationally altered proteins such as low-density lipoprotein receptor, cystic fibrosis transmembrane regulator, Huntingtin, A-beta peptide, prions, insulin-related amyloid, hemoglobin, alpha synuclein, rhodopsin, crystallins, and p53. In a preferred embodiment, methods of the invention use palindromic probes as otherwise described herein, preferably, for example, a palindromic 33_mer probe containing amino acid sequences 126-104 and 109-126 of the PrP$^{(Sc)}$ protein to detect prions in a sample. In a preferred embodiment, the probes are bound at each end to moieties that are optically distinct and detectable upon conformational conversion of the probes to a n-sheet structure.

In one embodiment, the invention provides a method for detecting conformationally altered proteins or prions in a sample comprising:

(a) reacting the sample with one or more α-helix or random coil conformational probes that interact with the ββ-sheet conformation insoluble proteins or prions in the sample and thereby (i) undergo a conformational conversion to a predominantly ββ-sheet conformation, and (ii) form detectable aggregates with the ββ-sheet conformation insoluble proteins or prions in the sample; and (b) detecting levels of detectable aggregates, wherein levels of detectable aggregates correlate to the levels of ββ-sheet conformation insoluble proteins or prions in the sample and the infectiousness of the sample.

The invention also provides kits that use these methods as well as methods of diagnosing whether a subject suffers from, or is predisposed to, a disease associated with conformationally altered proteins or prions.

A kit of the instant invention comprises one or more α-helix or random coil conformational probes that interact with ββ-sheet conformation insoluble proteins or prions in the sample and thereby (i) undergo a conformational conversion predominantly to ββ-sheet conformation, and (ii) form detectable aggregates with the ββ-sheet conformation insoluble proteins or prions in the sample. The kit may further include moieties that bind to, or are bound to, probe termini and that are optically detectable upon conformational conversion of the probe to a predominantly to ββ-sheet conformation, as well as instructions for using the kit, and solutions for suspending or fixing samples.

A method of diagnosing whether a subject suffers from, or is predisposed to, a disease associated with conformationally altered proteins or prion comprises:

(a) obtaining a sample from the subject;

(b) reacting the sample with one or more α-helix or random coil conformational probes that interact with the ββ-sheet conformation of insoluble proteins or prions in the sample and thereby (i) undergo a conformational conversion preferably to a predominantly ββ-sheet conformation, and (ii) form detectable aggregates with the ββ-sheet conformation insoluble proteins or prions in the sample; and (c) detecting levels of detectable aggregates, wherein levels of detectable aggregates correlate to the amount of the ββ-sheet conformation insoluble proteins or prions in, and level of infectiousness of, the sample and indicate whether the subject suffers from, or is predisposed to, a disease associated with ββ-sheet conformation insoluble proteins or prions.

These and other aspects of the invention are described further in the following detailed description.

BRIEF DESCRIPTION OF THE FIGURES

FIG. 2 illustrates a diagnostic analysis of a sample containing TSE protein comprised of beta-sheets 12.

1. pH 6-8, KCl (100-500 mM)
2. pH 10-11, KCl (100-500 mM)

Figure 16:
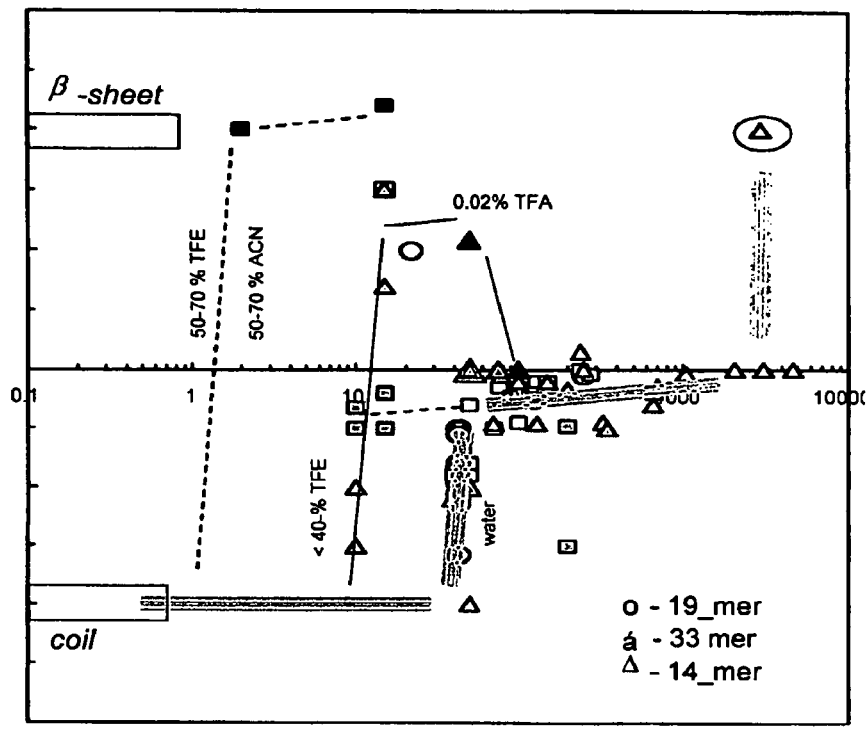

FIG. 16 illustrates an associative curve for conformation changes in a diagnostic analysis that used a palindromic 33_mer probe (SEQ ID NO: 1), the 19_mer (SEQ ID NO: 2) and 14_mer (SEQ ID NO: 3) (See FIG. 10) under various conditions to determine the optimal parameters associated with the transformation from coiled to β-sheet.

Figure 17:
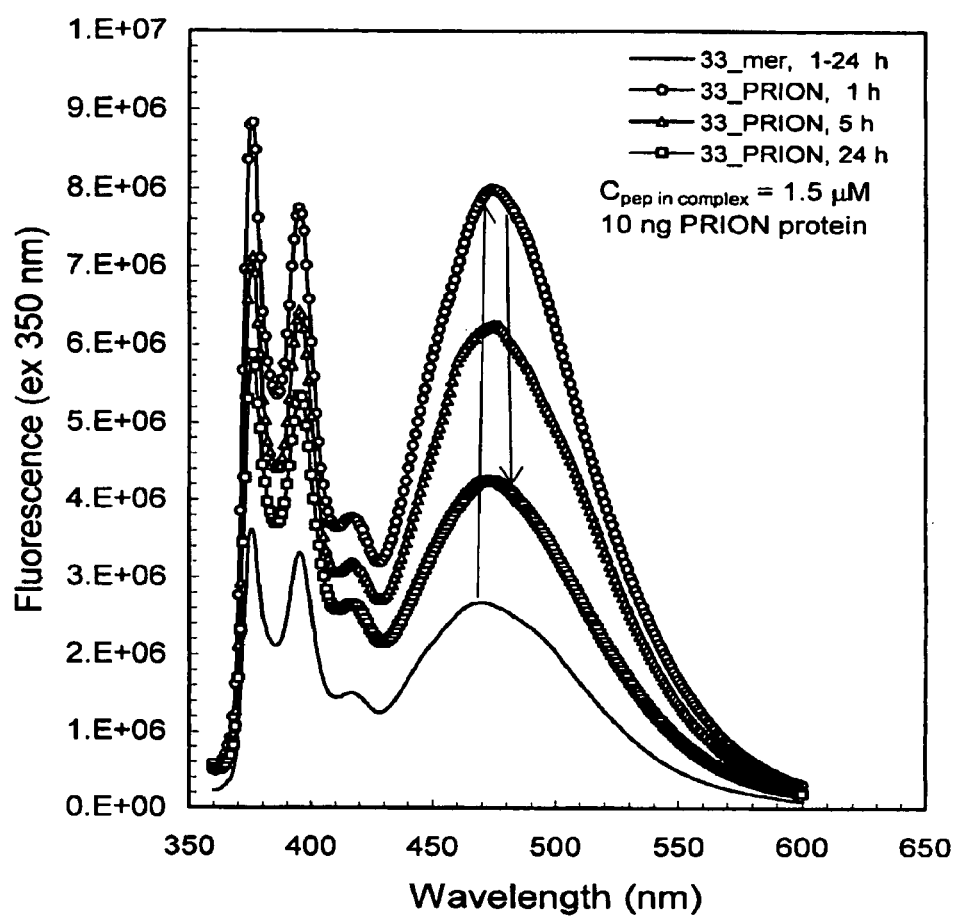

FIG. 17 shows the results from the experiment described in Example 6 wherein the fluorescence of a complex of prion protein and 33_mer probe was measured as a function of time. The complex substantially dissociated over time (1 hour-24 hours).

Figure 18:
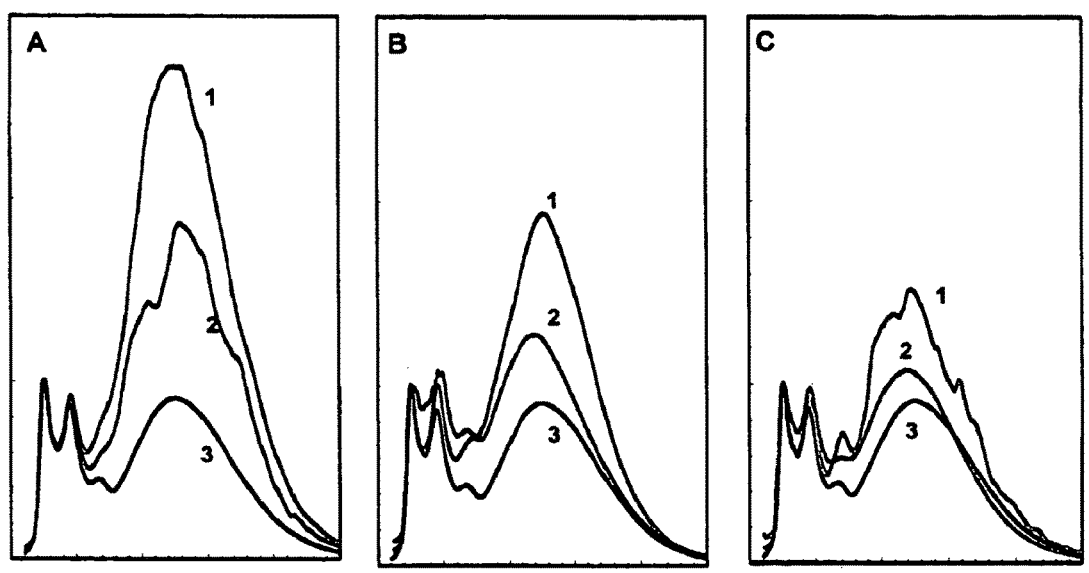

FIG. 18 (*a*)-(*c*) illustrate fluorescence spectra of target peptide [520 nM] in the presence of infected brain homogenate (1), healthy brain homogenate (2), and peptide alone (3) in TRIS:TFE (1:1) solvent. The data were obtained for 0.01% brain homogenate from hamster (A), sheep (B), and elk (C) (hamster [270 pg/ml], sheep [60 pg/ml], and elk [6 pg/ml]).

Figure 19:
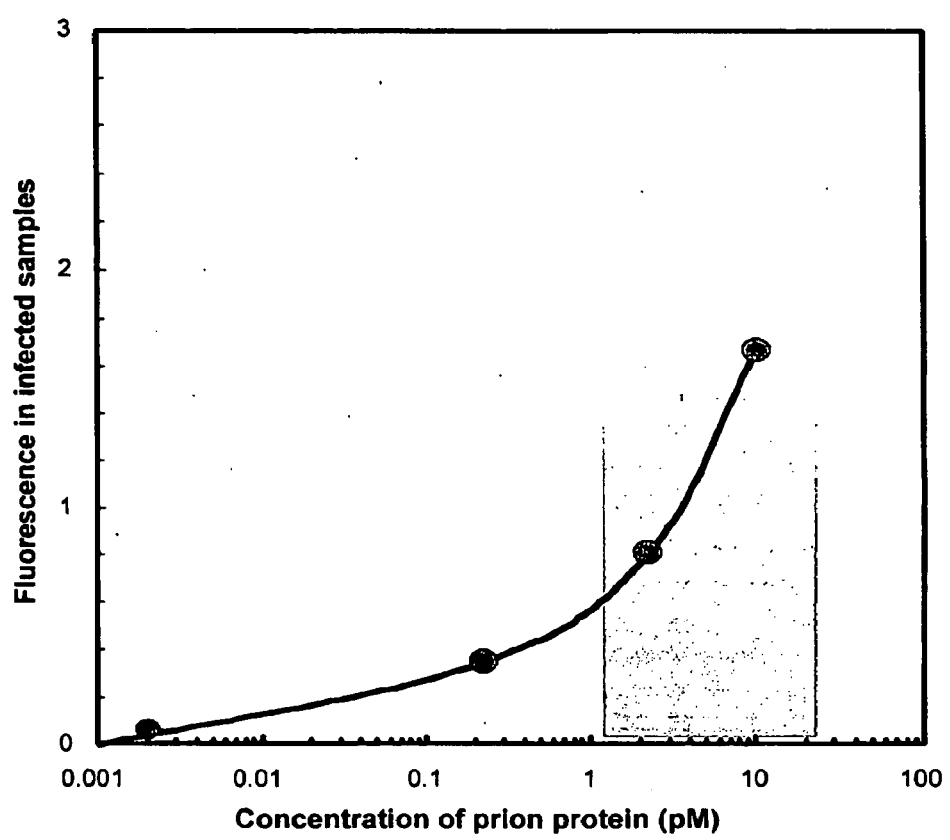

FIG. 19 illustrates a preliminary calibration curve of a fluorescent diagnostic analysis conducted in accordance with the invention. The data illustrated in this figure evidences that the present invention is more than two orders of magnitude more sensitive than the validated tests in use in Europe today without any optimization. Prion Infectivity: 1 IU=3 fM=200,000 PrP The prion protein concentration was determined using the capillary immunoelectrophoresis method of Dr. Schmerr. See, Schmerr, et al., *J. Chromatogr. A.*, 853 (1-2), 207-214 (Aug. 20, 1999). The sensitivity of the diagnostics with the present invention appears to the left of the green bar, whereas the sensitivity of more conventional diagnostics appears to the right of the green bar. The data are taken from FIG. 18.

DETAILED DESCRIPTION OF THE INVENTION

As used herein, the following terms have the following respective meanings.

"Amyloidogenic diseases" are diseases in which amyloid plaques or amyloid deposits are formed in the body. Amyloid formation is found in a number of disorders, such as diabetes, Alzheimer's Disease (AD), scrapie, Gerstmann-Straussler-Scheinker (GSS) Syndrome, bovine spongiform encephalopathy (BSE), Creutzfeldt-Jakob disease (CJD), chronic wasting disease (CWD), and related transmissible spongiform encephalopathies (TSEs).

TSE's are fatal neurodegenerative diseases that include such human disorders as CJD, kuru, fatal familial insomnia, and GSS. Animal forms of TSE include scrapie in sheep, CWD in deer and elk, and bovine spongiform encephalopathy in cattle. These diseases are characterized by the formation and accumulation in the brain of an abnormal proteinase K resistant isoform (PrP-res) of a normal protease-sensitive host-encoded prion protein (PrP-sen). PrP-res is formed from PrP-sen by a post-translational process involving conformational changes that convert the PrP-sen into a PrP-res molecular aggregate having a higher beta.-sheet content. The formation of these macromolecular aggregates of PrP-res is closely associated with TSE-mediated brain pathology in which amyloid deposits of PrP-res are formed in the brain, which eventually becomes "spongiform" (filled with holes).

TSE diseases appear to be transmitted by exposure to an unusual agent, for example by ritual cannibalism in the Foret people of New Guinea, or feeding of animal parts to cattle in bovine spongiform encephalopathy (BSE), iatrogenic CJD has also been caused by administration of human growth hormone derived from cadaveric pituitaries, transplanted dura mater and corneal grafts, as well as exposure of surgeons to affected tissue during neurological procedures.

The presence of a native prion protein (PrP) has been shown to be essential to pathogenesis of TSE. The cellular protein PrP-sen is a sialoglycoprotein encoded by a gene that in humans is located on chromosome 20. The PrP gene is expressed in neural and non-neural tissues, with the highest concentration of its mRNA being in neurons. The translation product of the PrP gene consists of 253 amino acids in humans, 254 in hamsters and mice, 264 amino acids in cows, and 256 amino acids in sheep (all of these sequences are disclosed in U.S. Pat. No. 5,565,186, which describes methods of making transgenic mice that express species specific PrP). In prion protein related encephalopathies, the cellular PrP-sen is converted into the altered PrP-res that is distinguishable from PrP-sen in that PrP-res aggregates (Caughey and Chesebro, 1997, Trends Cell Biol. 7, 56-62); are proteinase K resistant in that only approximately the N-terminal 67 amino acids are removed by proteinase K digestion under conditions in which PrP-sen is completely degraded (Prusiner et al., 1996, Sem. Virol. 7, 159-173); and has an alteration in protein conformation in which the amount of .alpha.-helical conformation for PrP-sen is reduced, and the amount of .beta.-sheet conformation for PrP-res is increased (Pan et al., 1993, Proc. Natl. Acad. Sci. USA 90, 10962-10966).

If PrP-sen is not expressed in the brain tissue of animal recipients of scrapie-infected neurografts, no pathology occurs outside the graft, demonstrating that PrP-res and PrP-sen are both required for the pathology (Brander et al., Nature 379:339-343, 1996). The long latency period between infection and the appearance of disease (months to decades depending on species) has prompted the development of a cell-free in vitro test, in which PrP-res induces the conversion of PrP-sen to PrP-res (Kocisko et al., Nature 370:471474, 1994). See also Prusiner et al., WO 97/16728 published May 9, 1997. These in vivo and in vitro observations indicate that direct interactions between PrP-res and PrP-sen form PrP-res and promote TSE pathogenesis.

Small synthetic peptides containing certain PrP sequences have previously been shown to spontaneously aggregate to form fibrils with a high degree of .beta.-sheet secondary structure of the type seen in the insoluble deposits in TSE afflicted brains (Gasset et al., 1992, Proc. Natl. Acad. Sci. USA 89, 10940-10944; Come et al., 1993, Proc. Natl. Acad. Sci. USA 90, 5959-5963; Forloni et al., 1993, Nature 362, 543-546; Hope et al., 1996, Neurodegeneration 5, 1-11). Moreover, other synthetic PrP peptides have been shown to interact with PrP-sen molecules to form an aggregated complex with increased protease-resistance (Kaneko et al., Proc. Natl. Acad. Sci. USA 92, 11160-11164, 1995; Kaneko et al., J. Mol. Biol. 270, 574-586, 1997).

"Conformationally altered proteins" include any protein which has a three dimensional conformation associated with a disease. The conformationally altered protein may cause the disease, may be a factor in a symptom of the disease, or may appear in a sample or in vivo as a result of other factors. A conformationally altered protein appears in another conformation which has the same amino acid sequence. These conformationally altered proteins are generally in the form of insoluble proteins exhibiting ββ-sheet formation which are analyzed in the present invention.

The following is a non-limiting list of diseases followed parenthetically by associated insoluble proteins which assemble into two or more different conformations wherein at least one conformation is an example of a conformationally altered protein: Alzheimer's Disease (APP, A.beta. peptide, alpha.1-antichymotrypsin, tau, non-A.beta. component, presenilin 1, presenilin 2 apoE); Prion diseases, Creutzfeld Jakob disease, scrapie and bovine spongiform encephalopathy ($PrP^{Sc}$); ALS (SOD and neurofilament); Pick's disease (Pick body); Parkinson's disease (alpha.-synuclein in Lewy bodies); Frontotemporal dementia (tau in fibrils); Diabetes Type II (Amylin); Multiple myeloma—plasma cell dyscrasias (IgGL-chain); Familial amyloidotic polyneuropathy (Transthyretin); Medullary carcinoma of thyroid (Procalcitonin); Chronic renal failure ($beta_2$-microglobulin); Congestive heart failure (Atrial natriuretic factor); Senile cardiac and systemic amyloidosis (Transthyretin);

Chronic inflammation (Serum amyloid A); Atherosclerosis (ApoA1); Familial amyloidosis (Gelsolin); Huntington's disease (Huntingtin).

An "insoluble protein" includes any protein associated with an amyloidogenic disease, including but not limited to any of the proteins identified in the preceding paragraph. Insoluble proteins generally exhibit ββ-sheet formation in the aggregate.

"PrP protein", "PrP" and like are used interchangeably herein and shall mean both the infectious particle form $PrP^{Sc}$ known to cause diseases (spongiform encephalopathies) in humans and animals and the noninfectious form $PrP^C$ which, under appropriate conditions is converted to the infectious $PrP^{Sc}$ form.

The terms "prion", "prion protein", "$PrP^{Sc}$ protein" and the like are used interchangeably herein to refer to the infectious $PrP^{Sc}$ form of a PrP protein. "Prion" is a contraction of the words "protein" and "infection." Particles are comprised largely, if not exclusively, of $PrP^{Sc}$ molecules encoded by a PrP gene. Prions are distinct from bacteria, viruses and viroids. Known prions infect animals and cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI). As used herein "prion" includes all forms of prions causing all or any of these diseases or others in any animals used—and in particular in humans and domesticated farm animals.

The term "PrP gene" is used herein to describe genetic material which expresses proteins including known polymorphisms and pathogenic mutations. The term "PrP gene" refers generally to any gene of any species which encodes any form of a prion protein. The PrP gene can be from any animal, and includes all polymorphisms and mutations thereof, it being recognized that the terms include other such PrP genes that are yet to be discovered. The protein expressed by such a gene can assume either a $PrP^C$ (non-disease) or $PrP^{Sc}$ (disease) form.

A "peptidomimetic" is a biomolecule that mimics the activity of another biologically active peptide molecule.

"Protein" refers to any polymer of two or more individual amino acids (whether or not naturally occurring) linked via a peptide bond, and occurs when the carboxyl carbon atom of the carboxylic acid group bonded to the .alpha.-carbon of one amino acid (or amino acid residue) becomes covalently bound to the amino nitrogen atom of amino group bonded to the α-carbon of an adjacent amino acid. These peptide bond linkages, and the atoms comprising them (i.e., .alpha.-carbon atoms, carboxyl carbon atoms (and their substituent oxygen atoms), and amino nitrogen atoms (and their substituent hydrogen atoms)) form the "polypeptide backbone" of the protein. In simplest terms, the polypeptide backbone shall be understood to refer the amino nitrogen atoms, .alpha.-carbon atoms, and carboxyl carbon atoms of the protein, although two or more of these atoms (with or without their substituent atoms) may also be represented as a pseudoatom. Indeed, any representation of a polypeptide backbone that can be used in a functional site descriptor as described herein will be understood to be included within the meaning of the term "polypeptide backbone."

The term "protein" is understood to include the terms "polypeptide" and "peptide" (which, at times, may be used interchangeably herein) within its meaning. In addition, proteins comprising multiple polypeptide subunits (e.g., DNA polymerase III, RNA polymerase II) or other components (for example, an RNA molecule, as occurs in telomerase) will also be understood to be included within the meaning of "protein" as used herein. Similarly, fragments of proteins and polypeptides are also within the scope of the invention and may be referred to herein as "proteins."

"Conformation" or "conformational constraint" refers to the presence of a particular protein conformation, for example, an alpha-helix, parallel and antiparallel beta. strands, leucine zipper, zinc finger, etc. In addition, conformational constraints can include amino acid sequence information without additional structural information. As an example, "—C—X—X—C—" is a conformational constraint indicating that two cysteine residues must be separated by two other amino acid residues, the identities of each of which are irrelevant in the context of this particular constraint. A "conformational change" is a change from one conformation to another.

The exact mechanism by which the sequence of a protein encodes the proper fold is unknown. In order to achieve the native state encoded by the fold, the protein molecule must convert to a unique conformation selected from many alternatives. Functional proteins are typically soluble and can adopt a variety of structures including coils and ordered elements. Ordered elements include the alpha helix predominant in proteins such as myoglobin and hemoglobin. During the human aging process, in some proteins the soluble structure (e.g. alpha helical regions) becomes conformationally altered into beta sheet structures that undergo aggregation associated with loss of function.

Figure 1:
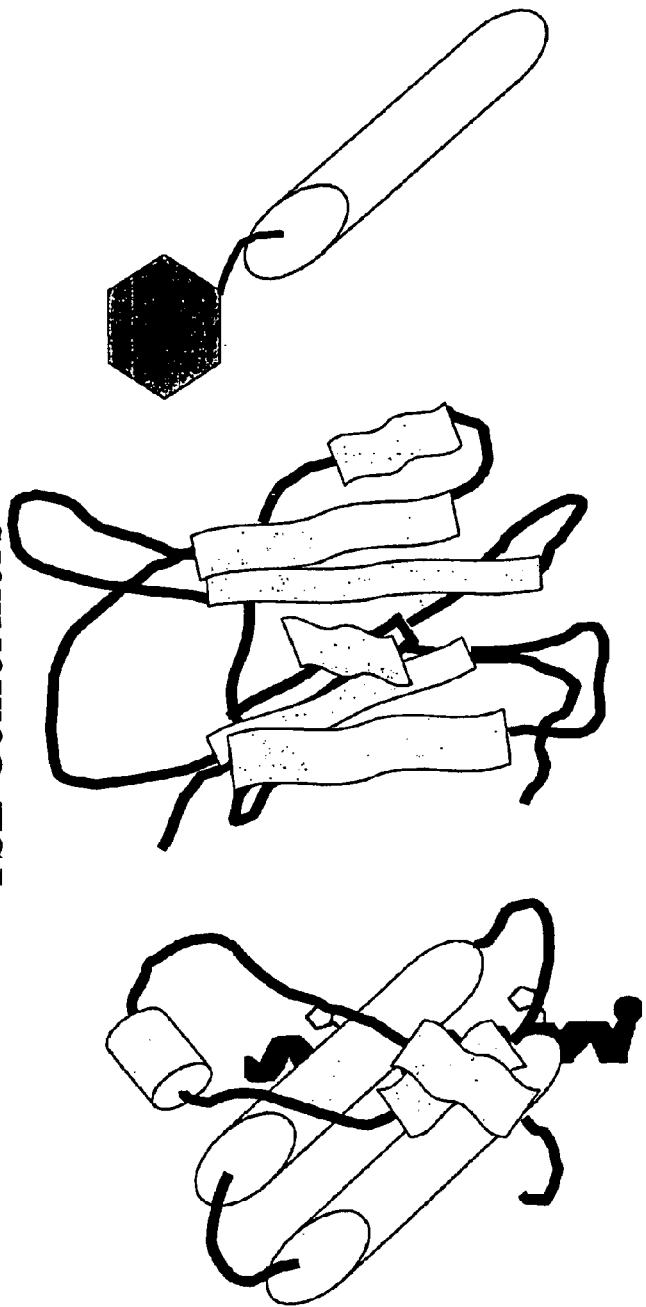
FIG. 1 illustrates the alpha-helical monomer 10 and beta-sheet dimer 12 of a TSE conformer. The normal wild-type (wt) form of prion protein (PrP$^C$) prefers a monomeric state, while the abnormal, disease-causing form (PrP$^{Sc}$) prefers the multimeric state.

There are at least twenty proteins that are associated with human disease when they adopt a conformationally altered state, and some of these have been described previously. FIG. 1 illustrates both the alpha-helical monomer 10 and the beta-sheet dimer 12 forms of a TSE conformer. The normal wild-type (wt) form of prion protein ($PrP^C$) prefers a monomeric state, while the abnormal, disease-causing form ($PrP^{Sc}$) more readily takes on a multimeric state.

Protein structures can be determined by a variety of experimental or computational methods, several of which are described below. Protein structure can be assessed experimentally by any method capable of producing at least low resolution structures. Such methods currently include X-ray crystallography and nuclear magnetic resonance (NMR) spectroscopy. X-ray crystallography is one method for protein structural evaluation, and is based on the diffraction of X-ray radiation of a characteristic wavelength by electron clouds surrounding the atomic nuclei in the crystal. X-ray crystallography uses crystals of purified biomolecules (but these frequently include solvent components, co-factors, substrates, or other ligands) to determine near atomic resolution of the atoms making up the particular biomolecule. Techniques for crystal growth are known in the art, and typically vary from biomolecule to biomolecule. Automated crystal growth techniques are also known.

Nuclear magnetic resonance (NMR) currently enables determination of the solution conformation (rather than crystal structure) of biomolecules. Typically only small molecules, for example proteins of less that about 100-150 amino acids, are amenable to these techniques. However, recent advances have lead to the experimental elucidation of the solution structures of larger proteins, using such techniques as isotopic labeling. The advantage of NMR spectroscopy over X-ray crystallography is that the structure is determined in solution, rather than in a crystal lattice, where lattice neighbor interactions can alter the protein structure. The disadvantage of NMR spectroscopy is that the NMR structure is not as detailed or as accurate as a crystal structure. Generally, biomolecule structures determined by NMR spectroscopy are of moderate resolution compared relative to those determined by crystallography.

Other techniques useful in studying biomolecule structure include circular dichroism (CD), fluorescence, and ultraviolet-visible absorbance spectroscopy. See, for example, *Physical Biochemistry: Applications to Biochemistry and Molecular Biology*, 2.sup.nd ed., W.H. Freeman & Co., New York, N.Y., 1982 for descriptions of these techniques.

"Equivalent" refers to amino acid sequences that are similar in sequence to the amino acid sequence of the protein to be analyzed but have at least one, but fewer than 5, (e.g., 3 or fewer) differences, substitutions, additions, or deletions. Thus, the substitution of one or more amino acid in a given sequence which does not substantially change the basic function of that amino acid within its use in context, is an equivalent for purposes of describing the present invention.

"Homology", "homologs of", "homologous", or "identity" or "similarity" refers to sequence similarity between two polypeptides, with identity being a more strict comparison. Homology and identity can each be determined by comparing a position in each sequence which may be aligned for purposes of comparison. When a position in the compared sequence is occupied by the same amino acid, then the molecules are identical at that position. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares less than 40% identity, though preferably less than 25% identity, with one of the sequences used in the present invention. Related sequences share more than 40% identity, preferably at least about 50% identity, more preferably at least about 70% identity, even more preferably at least about 90% identity, more preferably at least about 99% identity.

The term "percent identical" refers to sequence identity between two amino acid sequences. Identity can each be determined by comparing a position in each sequence which may be aligned for purposes of comparison. When an equivalent position in the compared sequences is occupied by the same amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid mismatch between the two sequences. Other techniques for determining sequence identity are well-known and described in the art.

The term "interact" as used herein is meant to include detectable interactions (e.g., biochemical interactions) between molecules, such as interaction between protein-protein, protein-nucleic acid, nucleic acid-nucleic acid, and protein-small molecule or nucleic acid-small molecule in nature.

The term "homolog of an insoluble protein" includes all amino acid sequences that are encoded by a homolog of an insoluble protein gene, and all amino acid sequences that are equivalent or homologous to such sequences. Therefore, "homolog of an insoluble protein" includes proteins that are scored as hits in the Pfam family. To identify the presence of an "insoluble protein" domain in a protein sequence, and make the determination that a polypeptide or protein of interest has a particular profile, the amino acid sequence of the protein can be searched against one of several databases (SwissProt, PIR, for example) using various default parameters (http://www.sanger.ac.uk/Software/Pfam/HMM_search). For example, the hmmsf program, which is available as part of the HM_MER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonham_mer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference.

"Test specimen" is a sample of material to be tested. The sample may be prepared from tissue (e.g. a portion of ground meat, an amount of tissue obtained by a biopsy procedure) by homogenization in a glass homogenizer. The amount of material should be between about 1 mg and 1 gm, preferably between 10 mg and 250 mg, ideally between 20 and 100 mg. The material to be sampled may be suspended in a suitable solvent, preferably phosphate-buffered saline at a pH between 7.0 and 7.8. The solvent may contain a detergent such as (Triton X-100, SDS, or sarkosyl). Homogenization is performed for a number of excursions of the homogenizer, preferably between 10 and 25 strokes; ideally between 15 and 20 strokes. The suspended sample is preferably centrifuged at between 100 and 1,000 g for 5-10 minutes and the supernatant material sampled for analysis. In some samples, it may be preferable to treat the supernatant material with an additional reagent such as phosphotungstic acid according to the procedure described by Safar et al., *Nature Medicine* 4, pp. 1157-1165 (1998) and as modified by Wadsworth et al. *The Lancet,* 358, pp. 171-180 (2001).

The amount of sample to be tested is based on a determination of the protein content of the supernatant solution as measured by the procedure described by Bradford (1976). Preferably, this corresponds to between 0.5 and 2 mg of protein.

In addition to the procedure described above for tissue material, test samples may be obtained from serum, pharmaceutical formulations that may contain products of animal origin, spinal fluid, saliva, urine or other bodily fluids. Liquid samples may be tested directly or may be subjected to treatment with agents such as phosphotungstic acid as described above.

"Conformational probes" are preferably peptides that have amino acid sequences that are similar to, and more preferably identical to, some of those in the target protein and that also have the potential to undergo conformational alteration to produce $\beta\beta$-sheet formation when complexed with the target protein (insoluble protein). Such alteration typically leads to a β sheet structure not normally evidenced by the probe. Ideally, a probe has a palindromic structure with two amino acid sequences derived from the target protein. Preferred α-helix or random coil conformational probes (i.e., probes that exhibit α-helix or random coil conformation in solution) useful in the instant invention include the following:

a palindromic 33_mer comprising amino acid sequences that are identical to amino acids 122-104 and 109-122 of the PrP$^{SC}$ protein (SEQ ID NO: 13 and 14) (Swiss-Prot PO4156 (Pfam ID Prion Pf00377 & 03991)

```
            (murine)
                                       SEQ ID NO: 29
    VVAGAAAAGAVHKLNTKPKLKHVAGAAAAGAVV (human)
                                       SEQ ID NO: 1
    VVAGAAAAGAMHKMNTKPKMKHMAGAAAAGAVV;
``` a palindromic 33_mer comprising amino acid sequences that are equivalent to amino acids 122-104 and 109-122 of the PrP$^{SC}$ protein SEQ ID NO: 13 and 14) (Swiss-Prot PO4156 (Pfam ID Prion Pf00377 & 03991)

```
            (murine)
                                       SEQ ID NO: 29
    VVAGAAAAGAVHKLNTKPKLKHVAGAAAAGAVV (human)
                                       SEQ ID NO: 1
    VVAGAAAAGAMHKMNTKPKMKHMAGAAAAGAVV;
``` a palindromic 33_mer comprising amino acid sequences that are between about 70% to about 90% identical to amino acids 122-104 and 109-122 of the PrP$^{SC}$ protein SEQ ID NO: 13 and 14) (Swiss-Prot PO4156 (Pfam ID Prion Pf00377 & 03991)

```
            (murine)
                                       SEQ ID NO: 29
    VVAGAAAAGAVHKLNTKPKLKHVAGAAAAGAVV (human)
    VVAGAAAAGAMHKMNTKPKMKRMAGAAAAGAVV
``` a probe comprising amino acid sequences that are identical to amino acids 1-40 of the Abeta peptide (Nref 00111747 (human))

```
                                       (SEQ ID NO: 4)
    DAEFRHDSGYEVHHQKLVFFAEDVGSNKGAIIGLMVGGVV;
``` a probe comprising amino acid sequences that are equivalent to amino acids 1-40 of the Abeta peptide (Nref 00111747 (human))

```
                                       (SEQ ID NO: 4)
    DAEFRHDSGYEVHHQKLVFFAEDVGSNKGAIIGLMVGGVV;
``` a probe comprising amino acid sequences that are between about 70% to about 90% identical to amino acids 1-40 of the Abeta peptide (Nref 00111747 (human))

```
                                       (SEQ ID NO: 4)
    DAEFRHDSGYEVHHQKLVFFAEDVGSNKGAIIGLMVGGVV;
``` a probe comprising amino acid sequences that are identical to amino acids 11-34 of the Abeta peptides (Nref 00111747 (human))

```
                                       (SEQ ID NO: 5)
    EVHHQKLVFFAEDVGSNKGAIIGL;
``` a probe comprising amino acid sequences that are identical to amino acids 11-34 of the Abeta peptides (Nref 00111747 (human)) but with residue H13 substituted with R to reduce metal ion interactions and to increase the solubility of the peptide

```
                                       (SEQ ID NO: 6)
    EVRHQKLVFFAEDVGSNKGAIIGL;
``` a probe comprising amino acid sequences that are identical to amino acids 25-35 of the Abeta peptides (Nref 00111747 (human))

```
                                       (SEQ ID NO: 7)
    GSNKGAIIGLM;
``` a probe that has a helix-loop-helix conformation found in polylysine and an amino acid sequence that is at least 10 amino acid residues in length and is equivalent or homologous to SEQ ID NO:8

```
                                       (27_mer)
    KKKKKKKKKKKKKKKKKKKKKKKKKKK;
``` a probe that has a conformation found in polyglutamine and an amino acid sequence that is equivalent or homologous to SEQ ID NO:9

```
    QQQQQQQQQQQQQQQQQQQQQQQQ;
``` a probe comprising amino acid sequences that are homologous to amino acids 104-122 of wild-type (wt) TSE (Human NREF 00130350)

```
                                       (SEQ ID NO: 10)
    KPKTNLKHVAGAAAAGAVV;
``` a probe comprising amino acid sequences that are equivalent to amino acids 104-122 of wild-type (wt) TSE (Human NREF 00130350)

```
                                       (SEQ ID NO: 10)
    KPKTNLKHVAGAAAAGAVV;
``` a probe comprising amino acid sequences that are between about 70% to about 90% identical to amino acid sequences 104-122 of wild-type (wt) TSE (Human NREF 00130350)

```
                                       (SEQ ID NO: 10)
    KPKTNLKHVAGAAAAGAVV;
``` a probe that comprise an amino acid sequence that: (a) is a selectively mutated TSE sequence; (b) is destabilized and noninfectious; and (c) has an amino acid sequence that is homologous to amino acid sequences 104-122 of wild-type (wt) TSE (Human NREF 00130350)

KPKTNLKHVAGAAAAGAVV; (SEQ ID NO: 10)

a probe that comprise an amino acid sequence that: (a) is a selectively mutated TSE sequence; (b) is destabilized and noninfectious; and (c) has an amino acid sequence that is equivalent to amino acid sequences 104-122 of wild-type (wt) TSE (Human NREF 00130350)

KPKTNLKHVAGAAAAGAVV; (SEQ ID NO: 10)

a probe that comprise an amino acid sequence that: (a) is a selectively mutated TSE sequence; (b) is destabilized and noninfectious; and (c) has an amino acid sequence that is between about 70% to about 90% identical to amino acid sequences 104-122 of wild-type (wt) TSE (Human NREF 00130350)

KPKTNLKHVAGAAAAGAVV; (SEQ FD NO: 10)

a probe comprising amino acid sequences that are identical to amino acids 1-38 of the human islet amyloid polypeptide precursor (amylin) protein (Accession #NP_000406 (human) implicated in human diabetes

MGILKLQVFLIVLSVALNHLKATPIESHQVEKRKCNTA; (SEQ ID NO: 11)

a probe comprising amino acid sequences that are identical to at least 10 contiguous amino acid residues within the sequence corresponding to amino acids 1-38 of the human islet amyloid polypeptide precursor (amylin) protein (Accession #NP_000406 (human) implicated in human diabetes

MGILKLQVFLIVLSVALNHLKATPIESHQVEKRKCNTA; (SEQ ID NO: 11)

a probe comprising amino acid sequences that are identical to amino acids 1-25 of the human lung surfactant protein (NCBI Accession # AAH32785 (human) implicated in human infant SIDS

MAESHLLQWLLLLLPTLCGPGTAAW; (SEQ ID NO: 12)

a probe comprising amino acid sequences which include at least 10 contiguous amino acid residues of amino acids 104-122 of the human or amino acids 103-121 of the murine $PrP^{SC}$ protein (SEQ ID NO: 13 and 14) (Swiss-Prot PO4156 (Pfam ID Prion Pf00377 & 03991)

```
Human prion protein
Accession:  PO4156 (SEQ ID NO:  13)
            10         20         30         40         50         60
            |          |          |          |          |          |
MANLGCWMLV  LFVATWSDLG LCKKRPKPGG WNTGGSRYPG QGSPGGNRYP PQGGGGWGQP 70         80         90        100        110        120
            |          |          |          |          |          |
HGGGWGQPHG  GGWGQPHGGG WGQPHGGGWG QGGGTHSQWN KPSKPKTNMK HMAGAAAAGA 130        140        150        160        170        180
            |          |          |          |          |          |
VVGGLGGYML  GSAMSRPIIH FGSDYEDRYY RENMHRYPNQ VYYRPMDEYS NQNNFVHDCV 190        200        210        220        230        240
            |          |          |          |          |          |
NITIKQHTVT  TTTKGENFTE TDVKMMERVV EQMCITQYER ESQAYYQRGS SMVLFSSPPV

250
            |
ILLISFLIFL  IVG

#2 Mouse prion protein

Accession:  PO4925 (SEQ ID NO:  14)
            10         20         30         40         50         60
            |          |          |          |          |          |
manlgywlla  lfvtmwtdvg lckkrpkpgg wntggsrypg qgspggnryp pqggtwgqph 70         80         90        100        110        120
            |          |          |          |          |          |
gggwgqphgg  swgqphggsw gqphgggwgq gggthnqwnk pskpktnlkh vagaaaagav 130        140        150        160        170        180
            |          |          |          |          |          |
vgglggymlg  samsrpmihf gndwedryyr enmyrypnqv yyrpvdqysn qnnfvhdcvn 190        200        210        220        230        240
            |          |          |          |          |          |
itikqhtvtt  ttkgenftet dvkmmervve qmcvtqyqke sqayydgrrs sstvlfsspp 250
            |
villisflif  livg ;
``` a probe comprising amino acid sequences which include at least 10 contiguous amino acid residues of amino acids 235-269 (emphasized below) of the human plasma gelsolin (SEQ ID NO: 15) (P06396), Maury, et al. *FEBS Lett.*, 260(1), pp. 85-87 (1990);

```
  1 maphrpapal lcalslalca lslpvraata srgasqagap qgrvpearpn smvvehpefl 61 kagkepglqi wrvekfdlvp vptnlygdff tgdayvilkt vqlrngnlqy dlhywlgnec 121 sqdesgaaai ftvqlddyln gravqhrevq gfesatflgy fksglkykkg gvasgfkhvv 181 pnevvvqrlf qvkgrrvvra tevpvswesf nngdcfildl gnnihqwcgs nsnryerlka 241 tqvskgirdn ersgrarvhv seegtepeam lqvlgpkpal pagtedtake daanrklakl 301 ykvsngagtm svslvadenp faqgalksed cfildhgkdg kifvwkgkqa nteerkaalk 361 tasdfitkmd ypkqtqvsvl peggetplfk qffknwrdpd qtdglglsyl sshianverv 421 pfdaatlhts tamaaqhgmd ddgtgqkqiw riegsnkvpv dpatyggfyg gdsyiilyny 481 rhggrqgqii ynwqgaqstq devaasailt aqldeelggt pvqsrvvqgk epahlmslfg 541 gkpmiiykgg tsreggqtap astrlfqvra nsagatrave vlpkagalns ndafvlktps 601 aaylwvgtga seaektgaqe llrvlraqpv qvaegsepdg fwealggkaa yrtsprlkdk 661 kmdahpprlf acsnkigrfv ieevpgelmq edlatddvml ldtwdqvfvw vgkdsqeeek 721 tealtsakry ietdpanrdr rtpitvvkqg feppsfvgwf lgwdddywsv dpldramael 781 aa
```

YERLKATQVSKGIRDNERSGRARVHVSEEGTEPEAM (SEQ ID NO: 16);

a probe comprising amino acid sequences which include at least 10 contiguous amino acid residues of amino acids 27-146 (emphasized below) of the cytastain C protein sequence depicted below (SEQ ID NO: 17) (P01034), Levy, et al. *J. Exp. Med.*, 169(5), pp. 1771-8 (1989). The amyloid forming version of the peptide is 120 amino acids corresponding to amino acid residues 27-146 below. An appropriate probe is any portion thereof of at least 10 amino acids, numerous probes can be posited accordingly;

```
  1 magplrapll llailavala vspaagsspg kpprlvggpm dasveeegvr raldfavgey 61 nkasndmyhs ralqvvrark qivagvnyfl dvelgrttct ktgpnldncp fhdqphlkrk 121 afcsfqiyav pwqgtmtlsk stcqda
```

Palindromic probe of cystatin C protein (from amino acids 39-47 of the above sequence with a four unit proline linker)
EEEVSADMPPPPMDASVEEE ((SEQ ID NO: 18)

a probe comprising amino acid sequences which include at least 10 and up to 23 contiguous glutamine amino acid residues oligo or polyglutamine (from residues 18-40) of the Huntingtin (Huntington's Disease Protein) protein sequence depicted below (SEQ ID NO: 19) (P42858) [gi:1170192]:

```
1
    matleklmka feslksfqqq qqqqqqqqqq qqqqqqqqqq pppppppppp pqlpqpppqa 61 qpllpqpqpp ppppppppgp avaeeplhrp kkelsatkkd rvnhcltice nivaqsvrns 121 pefqkllgia melfllcsdd aesdvrmvad eclnkvikal mdsnlprlql elykeikkng 181 aprslraalw rfaelahlvr pqkcrpylvn llpcltrtsk rpeesvqetl aaavpkimas 241 fgnfandnei kvllkafian lksssptirr taagsavsic qhsrrtqyfy swllnvllgl 301 lvpvedehst llilg............  . .
``` exemplary probe:

QQQQQQQQQQQQQQQQQ; (SEQ ID NO: 20)

ESVFVLGALPPPPLAGLVFVSE. (SEQ ID NO: 27)

a probe comprising amino acid sequences which include at least 6 contiguous amino acid residues of amino acid residues 12-17 and 15-20 (emphasized below) of the (8-20) domain of the human islet amyloid polypeptide involved in fibrillogenesis, sequence depicted below (SEQ ID NO: 21) NP_000406 [gi:4557655] Scrocchi, et al., *J. Struct. Biol.*, 141(3), pp. 218-27 (2003).

Numerous other probes may be readily produced without undue experimentation using standard laboratory techniques and peptide and related chemical syntheses.

The native conformation of the probe is determined by one or more spectroscopic methods such as circular dichroism, Fourier transform infra-red, ultra-violet, nuclear magnetic resonance, or fluorescence, among others. This conformation in a solvent as described below should correspond

```
 1 mgilklqvfl ivlsvalnhl katpieshqv ekrkcntatc atqr|lanflv hss|nnfgail 61 sstnvgsnty gkrnavevlk replnylpl
```

Exemplary probes contain the following sequences which are minimal sequences within the sequence 8-20 of the above peptide sequence, which may be used without modification or may be used to form palindromic probes of the present invention:

LANFV; (SEQ ID NO: 22)

VFNALPPPPLANFV (palindromic probe); (SEQ ID NO: 23)

FLVHSS; (SEQ ID NO: 24)

SSHVLFPPPFLVHSS (palindromic probe); (SEQ ID NO: 25)

a probe comprising amino acid sequences which include at least 5 contiguous amino acid residues of amino acid residues 10-19 (emphasized below) of the peptide fragment of transthyretin, sequence depicted below (SEQ ID NO: 26) AAH20791 [gi:18089145] MacPhee and Dobson, *J. Mol. Biol.*, 297(5), pp. 1203-15 (2000)

to that of an alpha-helix or random coil (in circular dichroism, for example, the nature of the spectrum is indicative of the conformation).

The probe is modified to contain substituents that are detectable by optical means. Such substituents may include tryptophan (an amino acid), pyrene or similar fluorophores, all attached at or near the terminal positions of the peptide probes. Attachment of such fluorophores proceeds according to conventional chemical methods which are well-known in the art, preferably, but not necessarily through covalent attachment of the fluorophore to the probe. Ideally, the substituents have the capability to interact in such a manner as to produce a species known as an excimer. An excimer represents the interaction of two fluorophores that, upon excitation with light of a specific wavelength, emits light at a different wavelength which is also different in magnitude from that emitted by either fluorophore acting alone. Thus, structural alterations of the conformational probe that allow for the formation of such excimers can be detected by a change in optical properties. Such changes can be measured by known fluorimetric techniques, including UV, IR, CD, NMR, or fluorescence, among numerous others, depending upon the fluorophore attached to the probe. The magnitude

```
1   mashrllllc laglvfvsea gptgtgeskc plmvkvldav rgspainvav hvfrkaaddt 61  wepfasgkts esgelhgltt eeefvegiyk veidtksywk algispfheh aevvftands 121 gprrytiaal lspysystta vvtnpke;
``` a palindromic probe based upon the above referenced sequence (amino acid residues 10-19):

of these changes is related to the degree to which the probe has undergone the conformational alteration.

In another embodiment, the probe may be substituted with a radioactive material. Ideally, this should be positron emission of a sufficient energy to be detected by machines currently employed for this purpose. Such an entity would preferably contain oxygen-15 (an isotope of oxygen that decays by positron emission) or other radionuclide. In this embodiment, the radiolabeled probe may be injected into a patient and the binding of the probe to the protein target monitored externally.

A probe may comprise a peptide or peptidomimetic of at least five, preferably about ten or more amino acid residues that exhibits a random coil or alpha-helical conformation in solution. A peptide or peptidomimetic probe solvent may be aqueous and have a pH of between about 4 and about 10, preferably between about 5 and about 8, and may have an ionic strength of between about 0.05 and about 0.5 (when typically prepared with a chloride salt such as sodium chloride or potassium chloride). The solvent may also contain a percentage of a water-miscible organic material such as trifluoroethanol in amounts between about 30 to about 70% by volume, preferably between about 45 to about 60%. The solvent may be prepared with a suitable buffering system such as acetate/acetic acid, Tris, or phosphate.

Figure 10:
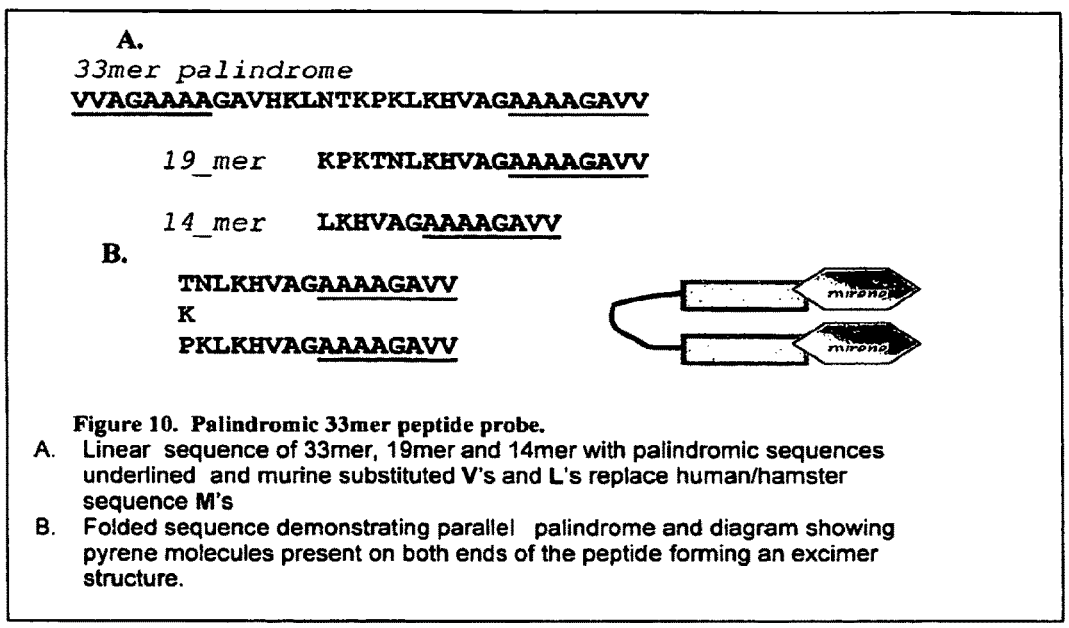
FIG. 10 illustrates a palindromic 33_mer probe used in the methods of the instant invention.

The sequence of probe amino acids is determined from the nature of the target protein to be analyzed and usually comprises a region of the target that is known to undergo a structural transition from either an alpha-helix or coil to a beta-sheet. This latter structure is associated with the pathogenic form of the target protein. The conformational probe sequence ideally contains two repeats of the target sequence of interest, preferably between about 10 and 25 amino acids in length; more preferably between about 14 and 20 amino acids in length. These are arranged preferably in the probe to form a palindrome as illustrated in FIG. 10.

Preferred probes used in methods and kits of the invention have amino acid sequences corresponding to β-sheet regions of the protein to be analyzed. These probes are preferably at least 5 amino acids units in length and can be about 300-400 amino acid units in length (_mer) or more, although, preferably these are about 10 amino acids to about 50 amino acids in length. In certain aspects of the invention, preferred probes which correspond to the β-sheet region are about 15 to about 100_mer, in others preferred probes may range from about 20 to about 50_mer. The preferred length of a given probe will be a function of the probes ability to complex and produce ββ-sheet formation with the target protein.

Probes for use in the present invention are readily determined from existing information in sequence databases already in existence or alternatively, may be readily determined experimentally. Thus, the probe will generally correspond to a minimum number of amino acids, preferably at least 10, and more preferably about 10 to 25 amino acids, which correspond to at least a portion of a peptide sequence of a target protein which undergoing a conformational transition from alpha-helix or random coil to ββ-sheet formation in the insoluble protein.

Noted that within the experimental information which will guide the presentation and synthesis of an appropriate probe, there are some constraints which can guide the practitioner in making use of the present invention. Because there are only a few kcal difference separating a population in the initial conformation state from a population predominantly in the transformed conformational state (in complex). This transformation is provided by the driving force due either to the Kd of association between the probe molecule and its natural associate to form ββ-sheet complex, or due to changes in the electrostatic interactions between the molecules (for example, by lowering the ionic strength of the solution. If metal ions such as Al are involved, or the binding of another ligand, other electrostatic or steric effects could contribute. The size of the probe peptide can vary, but should be of sufficient length to have "reasonably" well-defined secondary structure under detection conditions and to have sufficient recognitional specificity for the prion selected. The probe peptide should also accommodate single-site mutations in order to be generally applicable to mutated strains, recognizing that these changes and/or heterogeneities affect the thermodynamic stability of the molecule. Moreover, the probe must be non-contagious to the patient population, whether that population is a human patient population, a domesticated animal population or other mammalian population.

Once a peptide sequence is established for a probe (which corresponds to at least a portion of a target protein responsible for β-sheet formation as described above), the peptide sequence may be endcapped (at one, but preferably both ends of the peptide) with a moiety or chemical entity which can facilitate analysis of the peptide probe. Preferably, this moiety is a fluorophore, such as pyrene, but may vary widely, depending upon the analytical technique to be used for analysis. The moiety or chemical entity may be complexed or covalently bonded at or near the amino or carboxy end of the peptide, which is preferably endcapped with a short, hydrophobic peptide sequence. In preferred aspects of the present invention, both the amino and carboxy ends of the probe peptides are endcapped with small hydrophobic peptides ranging in size from about 1 to about 5 amino acids. These may be natural or synthetic, but are preferably natural (i.e., derived from a β-sheet formation region of a target protein. The fluorophore are preferably attached at or near the amino and/or carboxy end of the probe (preferably both) and may be, for example, pyrene, tryptophan, fluorescein, rhodamine, among numerous others and is preferably pyrene. It is preferable that the fluorophores form excimers when in the correct geometric orientation.

Conformational probes according to the present invention are preferably palindromic in nature. This refers to the organization of a given conformational probe sequence such that it will contain first and second peptide sequences corresponding to a portion of the target protein responsible for β-sheet formation, but which peptide sequences are presented in a palindromic manner, i.e., from the carboxy end to the amino end (or amino end to carboxy end) in the first peptide sequence, and from the amino end to the carboxy end (or carboxy end to amino end) in the second peptide sequence. The first and second peptide sequence in the palindromic conformational probe do not have to be identical in length, although this may be preferred in certain embodiments, but should be at least roughly equivalent (the two peptide sequences ("arms" of the probe) should not be more than 15, preferably no more than 10 and even more preferably no more than 5 amino acids different in length). Preferably, the first and second peptide sequences within a palindromic probe sequence are separated by a linker comprising between 1 and 5 amino acids, preferably between 1 and 3 amino acids, which preferably contain at least one proline amino acid and more preferably comprise primarily proline amino acids. FIG. 10 presents an exemplary palindromic 33_mer conformation probe useful in the present invention.

Preferably, conformational probes according to the present invention contain a hydrophobic amino acid sequence which is preferably derived from the relevant peptide sequence of the target protein (i.e., the peptide sequence responsible for β-sheet formation), and which may vary in length from 1 amino acid to 20 or more amino acids, preferably about 2-10 amino acids in length and appears at or near one of the two ends of the conformation probe. In the case of palindromic conformation probes, these hydrophobic amino acid sequences appear at the ends of the two peptide arms of the probe. Optionally, the probe also may contain a synthetic hydrophobic amino acid sequence (i.e., not natural to the peptide sequence of the target protein responsible for β-sheet formation) at at least one end of the probe and in the case of palindromic probes, at or near each end of the probe, which may vary in length from as few as one amino acid to 20 or more amino acids, preferably about 3-10 amino acids in length.

By way of example and without limitation, if a desired peptide sequence in a target protein contains the sequence, reading from amino end to carboxy end, QRSTVVURLKAAAV (SEQ ID NO:30) (where AAAV (SEQ ID NO:31) is a hydrophobic amino acid sequence) then the palindrome would contain a first peptide sequence which is VAAAKLRUWTSRQ (SEQ ID NO: 32) and a second peptide sequence which is QRSTWURLKAAAV (SEQ ID NO:30) (or a close variation to that sequence), with the two sequences separated by a linker comprising from 1 to 5 amino acids, with at least one of those amino acids, and preferably most, if not all, of those amino acids, being proline amino acids. The probe would therefore be:

```
                                        SEQ ID NO: 28
VAAAKLRUVVTSRQPPPPQRSTVVURLKAAAV
       (hypothetical palindromic probe)
```

Preferably, the palindromic probe would contain a hydrophobic amino acid sequence obtained from the relevant sequence of the target protein. Conformational probes according to the present invention may be readily obtained.

The following rules may be used to guide the formation of an appropriate preferred conformational probe according to the present invention. These rules apply generally to conformational probes according to the present invention without limitation, but are more specifically used in context to produce the preferred palindromic conformational probes according to the present invention.

The following rules may be applied to the instant invention to produce preferred conformational peptide probes:
1. Each "arm" of the peptide palindrome should have a minimum of five, and preferably at least 10-12 amino acids and, ideally, not more than about 25 amino acids.
2. The amino acid sequence is selected from a region of a larger protein that is known to undergo a conformational transition from alpha-helix or random coil to beta sheet.
3. One or more of the following additional criteria:
    a) A high proportion of hydrophobic amino acids— generally not less than about 75% (based upon the number of amino acids), ideally 80% or greater
    b) Amino acid repeats of at least 20 and preferably 25 (such as is present in huntingtin)
    c) Clustered charges of opposite sign (as described in Zhang, S., Altman, M. and Rich, A. in Conformational Disease, A Compendium, Solomon, Taraboulos and Katchalski-Katzir, eds. The Center for the Study of Emerging Diseases, 2001.
    d) A linker sequence between each of the peptide arms that has 1 or more amino acids, preferably less than five and that contains one or more proline residues Test criteria for peptide probe:
1. The conformation of the palindrome peptide probe should be that of an alpha helix or random coil but not a beta sheet.
2. Determination of the conformation of the peptide is ideally accomplished by circular dichroism measurements that can identify solution conformations. These are performed using a CD spectrometer in one or more solvents that can include aqueous buffers and/or organic agents such as trifluoroethanol—see FIG. 11.

Applying the general rules obtained above and using readily available methods in the art, one of ordinary skill can produce large numbers of conformational peptide probes having favorable characteristics to be useful in the present invention.

Figure 11:
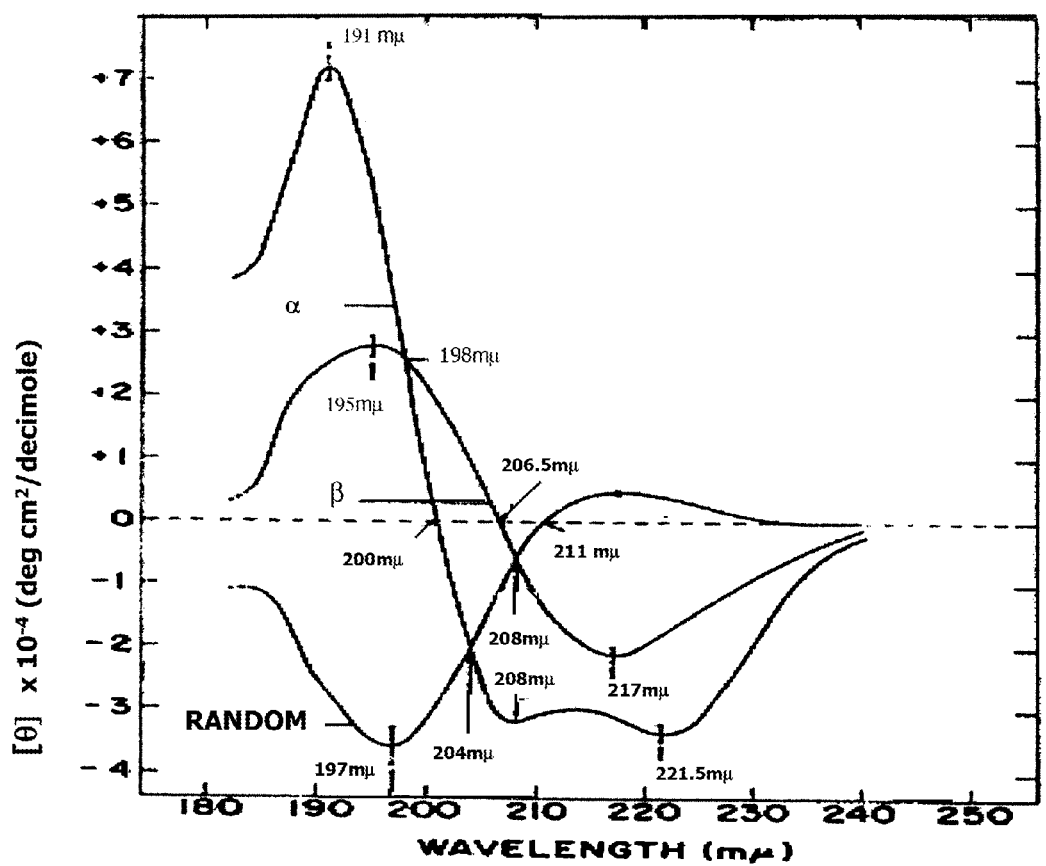
FIG. 11 illustrates a circular dichroism graph of three distinct common conformational forms that proteins and peptides can assume (source: Woody R W (1996) In *Circular Dichroism and the Conformational Analysis of Biomolecules* (Fasman, G D ed.) pp. 25-69, Plenum press NY).

"Circular dichroism" ("CD") is observed when optically active matter absorbs L and R hand circular polarized light slightly differently, as measured by a CD spectropolarimeter. Differences are very small and represent fractions of degrees in ellipticity. FIG. 11 depicts an associative CD curve representative of the three distinct common conformational forms that proteins and peptides can assume. CD spectra for distinct types of secondary structure present in peptides and proteins are distinct. Measuring and comparing CD curves of complexed vs uncomplexed protein represents an accurate measuring means of practicing the instant invention.

Figure 12:
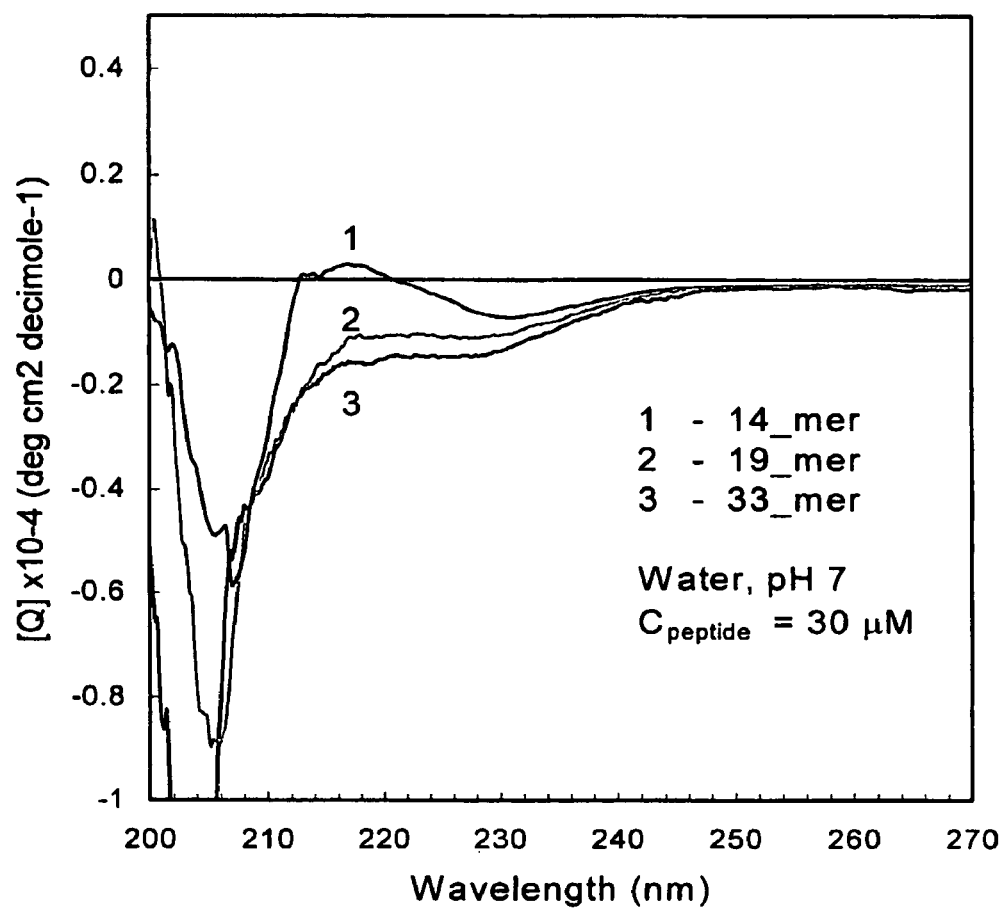
FIG. 12 illustrates a circular dichroism graph of a diagnostic analysis that was performed in aqueous conditions in accordance with the invention and that used a palindromic 33_mer probe and the 14_mer and the 19_mer amino acid sequences which make it up (these three sequences are set forth in FIG. 10).
Figure 13:
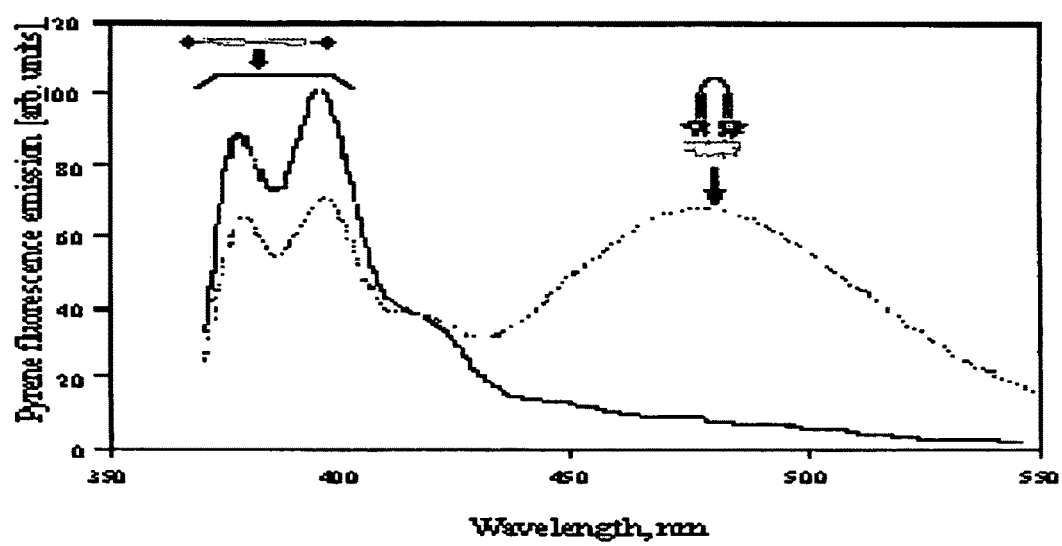
FIG. 13 illustrates a variation of the spectroscopic analysis of FIG. 6, in which a spectrofluorometric data of a diagnostic analysis that was performed using a palindromic 33_mer probe (SEQ ID NO: 1, SEE FIG. 10) that had pyrene attached to both ends. The spectral scans in the monomer (open) conformation yielded a strikingly fluorescent spectrum that had a maximum emission between 370 and 385 nm, while the excited dimer or excimer state of the pyrene-labeled peptide has an emission max between 475 and 510 nm.

Unexpectedly, we have determined that under near physiological conditions, the palindrome, 33_mer (SEQ ID NO: 1 or 29), which covalently connects two peptides—the 14_mer (SEQ ID NO: 3 and the 19_mer (SEQ ID NO:2) exhibits a largely coil conformation despite the proximity of two hydrophobic chains resembling the 14_mer structure, as illustrated in FIG. 12. The addition of a pyrene at each end of the palindromic 33_mer peptide allows for spectral observation of the conformational change, as illustrated in FIG. 13. The spectral scans for pyrene attached to the ends of the 33_mer in the monomer (open) conformation gives a strikingly different fluorescent spectrum, having a maximum emission between 370 and 385 nm, while the excited dimer or excimer state of the pyrene-labeled peptide has an emission max between 475 and 510 nm.

Although it is possible to follow conformational changes by any of the several optical methods described above, a preferred embodiment of the invention utilizes fluorescence spectroscopy since that technique provides sensitivity, rapidity and simplicity of operation. The probe is modified by attachment at both termini of a fluorophore that has specific optical properties. It is preferred that these include the ability to fluoresce upon irradiation with light of a specific wavelength (defined by the absorption and emission spectra of the chromophore itself). Thus, irradiation with light of a wavelength near that of the absorption maximum and emission of light at a sufficiently higher wavelength so as to be distinguished from the excitation wavelength—this measurement is well known to those versed in the art. Examples of such fluorophores include, but are not limited to, pyrene, tryptophan, fluorescein, rhodamine. It is also preferred that the attached fluorophores have the capacity to form excimers when in the correct geometric orientation.

An "excimer" is an adduct that is not necessarily covalent and that is formed between a molecular entity that has been excited by a photon and an identical unexcited molecular entity. The adduct is transient in nature and exists until it fluoresces by emission of a photon. It is possible to recognize an excimer (or the formation of an excimer) by the production of a new fluorescent band at a wavelength that is longer than that of the usual emission spectrum. An excimer can be distinguished from fluorescence resonance energy transfer since the excitation spectrum is identical to that of the monomer.

The formation of the excimer is dependent on the geometric alignment of the fluorophores and is heavily influenced by the distance between them. In a preferred embodiment, fluorophores are present at each probe terminus and excimer formation between fluorophores is negligible as long as the overall probe conformation is alpha-helix or random coil. This is readily determined by measurement of the fluorescent behavior of the probe in the solvent to be used for analysis in the absence of the target protein to be measured.

Preferred conformational transition following interaction with an analyte target is achieved by measuring fluorescence spectra under conditions where excimer formation can be analyzed. Typically, using pyrene as an exemplary fluorophor, the excitation wavelength would be about 350 nm and the observation wavelength 365-600 nm. The normal emission of monomer pyrene following excitation (simple fluorescence) is recorded as the maximum wavelength between about 370-385 nm. Representative data is shown in FIG. 14.

Figure 14:
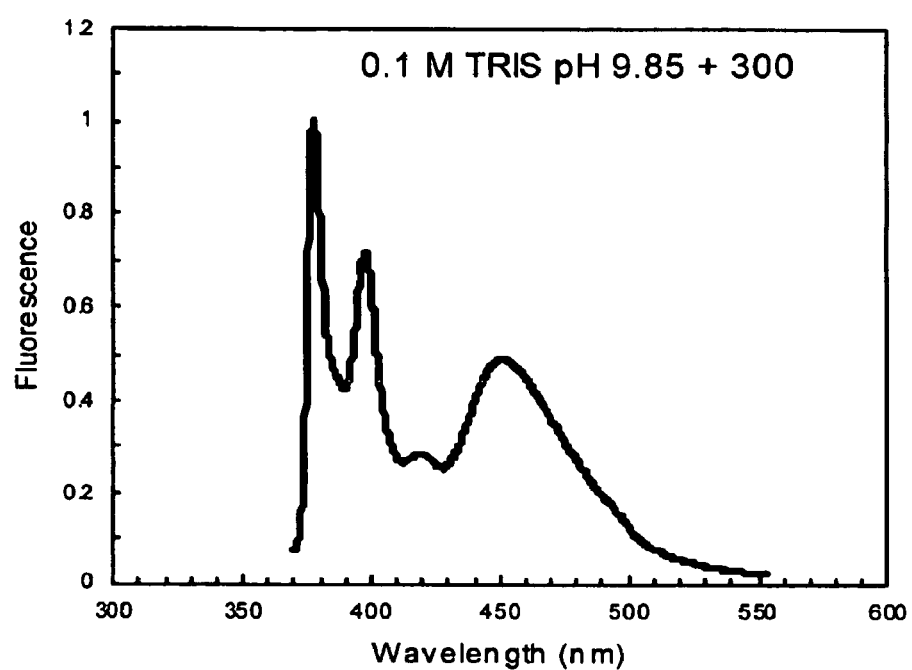
FIG. 14 illustrates a spectroscopic analysis in which pyrene was used as a fluorophor, the excitation wavelength was around 350 nm, and the observation wavelength was around 365-600 nm. The normal emission of monomer pyrene following excitation (simple fluorescence) was recorded as the maximum wavelength at between about 370-385 nm.

As shown in FIG. 14, the excimer or excited dimer state is recorded at a maximum of between 475-510 nm. The formation of the excited dimer state can also be encouraged through the addition of high salt and by conducting measurements at pH approaching the pI of the peptide (e.g., in the illustrated case, a pH of around 10).

Therefore, in a preferred method of the invention, interaction of the probe with the specific protein to be analyzed causes a conformational change in the probe such that excimer formation occurs. This is readily measured by the procedures described herein. Conversion of the probe structure from that exhibited in the absence of analyte (alpha-helix or random coil) to a beta-sheet structure enables fluorophores attached to the probe to form excimers that can be readily identified. Further, the magnitude of excimer formation is directly related to the amount of protein analyte present.

Proteins or prions may be detected in aggregated form or in the presence of other cellular constituents such as lipids, other proteins or carbohydrates. A sample preparation for analysis is preferably homogenized or subjected to a similar disruption of tissue or aggregate structures, and cellular debris is preferably removed by centrifugation. This process is ideally performed in the presence of a buffered salt solution and may utilize one of several detergents such as SDS, Triton X-100, or sarkosyl. Further concentration of the sample may be achieved by treatment with any of several agents; one preferred agent is phosphotungstate, which is employed according to the method of Safar et al *Nature Medicine* 4:1157-1165 (1998).

In a preferred embodiment of the invention, peptide probes are selected in order for addition to an unknown or test sample. The peptide probes are preferably proteins or peptide sequences that have secondary structures of predominately alpha-helix or random coil, but which are preferably, but not necessarily derived from portions of a target peptide responsible for β-sheet formation. In a particularly preferred embodiment, the peptide probes are peptide fragments consisting of a helix-loop-helix structure found in polylysine. In another particularly preferred embodiment, the peptide probes can be made of a peptide sequence chosen from wild-type (wt) TSE, from a desired species-specific TSE peptide sequence, or even from a selectively mutated TSE sequence that has been mutated in such a manner as to render it destabilized and noninfectious. Additionally, extrinsic fluors such as pyrene can be added or designed into the peptide probe to allow detection of anticipated conformational changes using common fluorescence detection techniques.

Once a peptide probe is selected, it is added to a test sample. Prior to the addition of the peptide probe, however, it is preferred to have the sample subjected to disaggregation techniques commonly known in the art, such as sonication. The disaggregation step allows any potentially aggregated sample material to break apart so that these disaggregated sample materials are free to combine with the newly introduced peptide probe, thereby facilitating the anticipated catalytic propagation.

After the test sample or disaggregated test sample is allowed to interact with the peptide probes, the resulting mixture is then subjected to analytical methods commonly known in the art for the detection of aggregates and to fluorescence measurements in cases where fluorescent peptide probes are used. Unknown or test samples containing any dominant beta-sheet formation characteristic of abnormally folded or disease-causing proteins result in an increase in beta-sheet formation and consequently aggregate formation in the final mixture containing both the test sample and the peptide probes. Conversely, unknown or test samples which lack a predominantly beta-sheet secondary structure will neither catalyze a transition to beta-sheet structure nor will propagate the formation of aggregates.

The initial conformational change can be triggered in the test samples in a number of ways. Without intending to be bound by any theory, the binding of a metal ligand could direct a change in the protein conformation and favor aggregation. The expression or cleavage of different peptide sequences can promote advanced aggregation leading to fibril and plaque formation. Genetic point mutations can also alter the relative energy levels required of the two distinct conformations, resulting in midpoint shifts in structural transitions. Furthermore, an increase in concentration levels could be sufficient to favor the conformational transition. Regardless of the initial trigger mechanism, however, the disease process in many of the abnormal protein conformations such as in prion-related diseases involves the catalytic propagation of the abnormal conformation, resulting in structural transformation of the previously normal protein.

Optical detection techniques useful in the instant invention include but are not limited to light scattering, or hydrophobicity detection using extrinsic fluors such as 1-anilino-8-napthalene sulfonate (ANS) or Congo Red stain, fluorescence resonance energy transfer (FRET) and quenching of intrinsic tryptophan fluorescence through either conformational change of monomer or binding at an interface in an alpha-beta heterodimer.

Other structural techniques include equilibrium ultracentrifugation or size-exclusion chromotography.

The instant invention uses propagated conformational change to correlate directly levels of abnormal proteins or prions with levels of infectivity. For this reason, it is preferable to utilize the methods of the invention in a manner in which there is no increase in infectious products as a result of the propagation. This can be achieved by placing a "break" in the links between the chain of infection, transmission, and propagation of the abnormal form. Such a "break" must occur at the transitional stage between the dimer and multimer forms of the aggregate. The physical formation of the multimer form can be blocked by simply impeding the step which leads to its formation. This may be achieved by using a probe in which the sequence of interest is attached to a non-relevant peptide, or by a neutral "blocker" segment, with the understanding that probes on linkers or "tethers" are more likely to encounter each other and thus result in amplifying the signal.

The invention is described further in the following examples, which are illustrative and in no way limiting.

EXAMPLE 1

Materials and Methods

A sample may be obtained for testing and diagnosis through use of the instant invention as follows. A sample may be prepared from tissue (e.g. a portion of ground meat, or an amount of tissue obtained by a biopsy procedure) by homogenization in a glass homogenizer or by mortar and pestle in the presence of liquid nitrogen. The amount of material should be between about 1 mg and 1 gm, preferably between 10 mg and 250 mg, ideally between 20 and 100 mg. The material to be sampled may be suspended in a suitable solvent, preferably phosphate-buffered saline at a pH between 7.0 and 7.8. The addition of Rnase inhibitors is preferred. The solvent may contain a detergent (e.g., Triton X-100, SDS, or sarkosyl). Homogenization is performed for a number of excursions of the homogenizer, preferably between 10 and 25 strokes; ideally between 15 and 20 strokes. The suspended sample is preferably centrifuged at between 100 and 1,000 g for 5-10 minutes and the supernatant material sampled for analysis. In some samples, it may be preferable to treat the supernatant material with an additional reagent such as phosphotungstic acid according to the procedure described by Safar et al., *Nature Medicine*, 4, 1157-1165 (1998) and as modified by Wadsworth, *The Lancet*, 358, 171-180 (2001). Eight prion strains have PrP$^{Sc}$ molecules with different conformations. See, Safar, et al. and Wadsworth, ibid. Tissue distribution of protease resistant prion protein in variant Creutzfeldt Jakob disease has been reported using a highly sensitive immunoblotting assay as described in Wadsworth, et al., ibid.

The amount of sample to be tested is based on a determination of the protein content of the supernatant solution as measured by the procedure described by Bradford, *Anal. Biochem.* 72:248-254 (1976). A rapid and sensitive method for determining microgram quantities of protein utilizes the principle of protein-dye binding. Preferably, this corresponds to between about 0.5 and 2 mg of protein.

In addition to the procedure described above for tissue material, test samples may be obtained from serum, pharmaceutical formulations that may contain products of animal origin, spinal fluid, saliva, urine or other bodily fluids. Liquid samples may be tested directly or may be subjected to treatment with agents such as phosphotungstic acid as described above.

Illustrative Analysis

Figure 2:
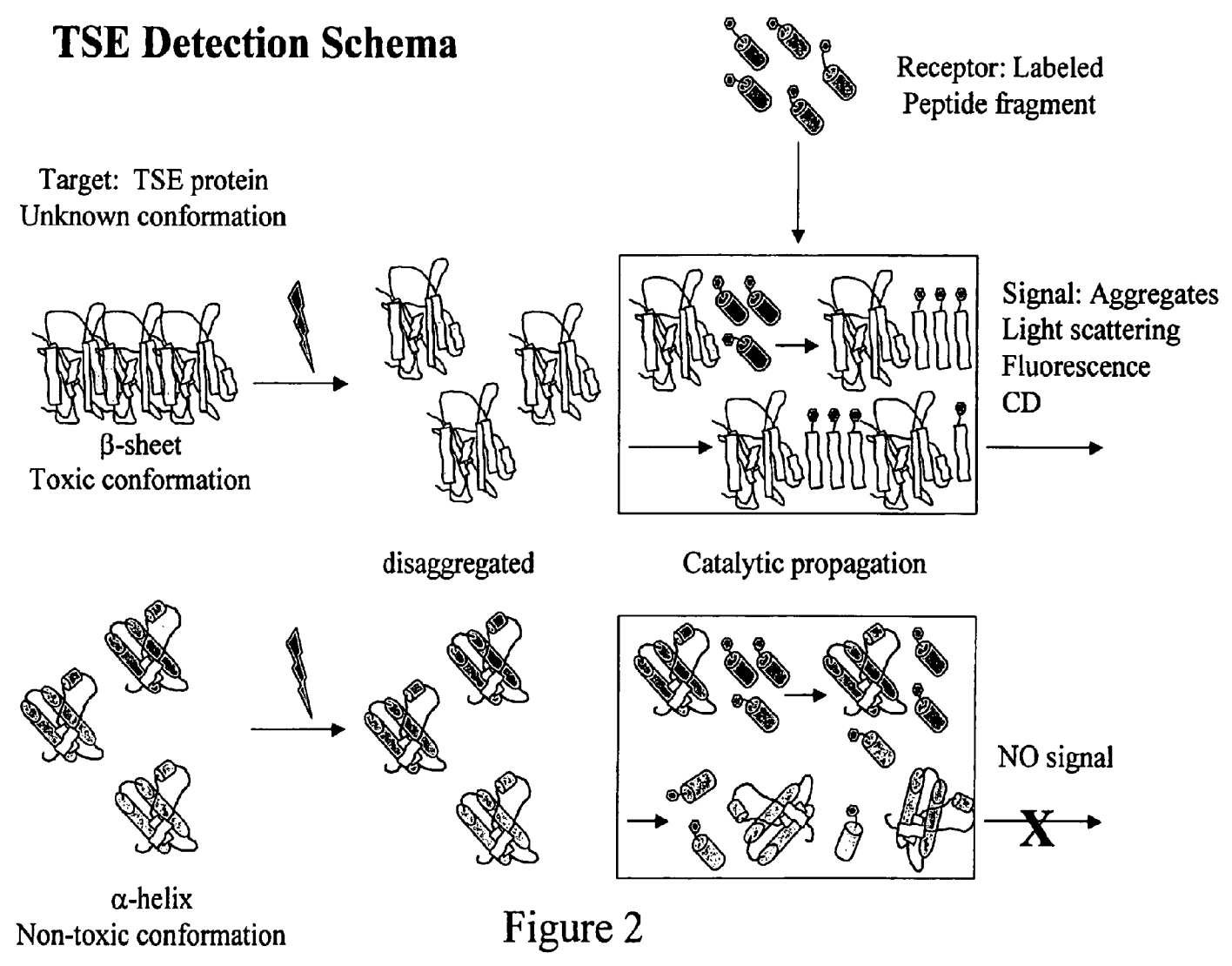

A sample containing TSE may be analyzed in accordance with the invention as follows. Referring to FIG. 2, the top row of the schematic illustrates an unknown sample of TSE protein represented as containing beta-sheets 12. The beta-sheets are disaggregated by sonication. Labeled peptide probes 14 are added and are allowed to bind to the sample 12. The beta-sheet conformation in sample 12 induces the peptide probes to conform to beta-sheet conformation 16. Beta-sheet propagation among the peptide probes 14 forms aggregates 18. The resulting transition to a predominately beta-sheet form and amplified aggregate formation is detected by techniques such as light scattering and circular dichroism (CD). In a particularly preferred embodiment, the peptide probe is fluorescently labeled and fluorescence detection is used.

The bottom row of FIG. 2 shows an alternative example in which the unknown sample of TSE protein is represented in its normal alpha-helical form 10. For consistency, the sample is subjected to the same disaggregation process described above. Upon addition of the labeled peptide probes 14, neither a transition to beta-sheet form nor binding to the unknown samples occurs. As a result, there is no aggregate fluorescence signal in the case of a labeled peptide probe and there is no detection of aggregate formation by other analytical tools. Based on this schematic, unknown samples can be tested for the presence or absence of such abnormal protein conformations or sequences.

EXAMPLE 2

Poly-lysine was used as a model peptide. Experiments were performed using model systems to illustrate the conformational changes involved in the transition from a predominately alpha-helix to a beta-rich form. The model system chosen used non-neurotoxic polyamino acid polylysine. The polyamino acid was chosen because of availability and safety; and normally evidences random coil conformation at pH values between 5 and 9.

Figure 3:
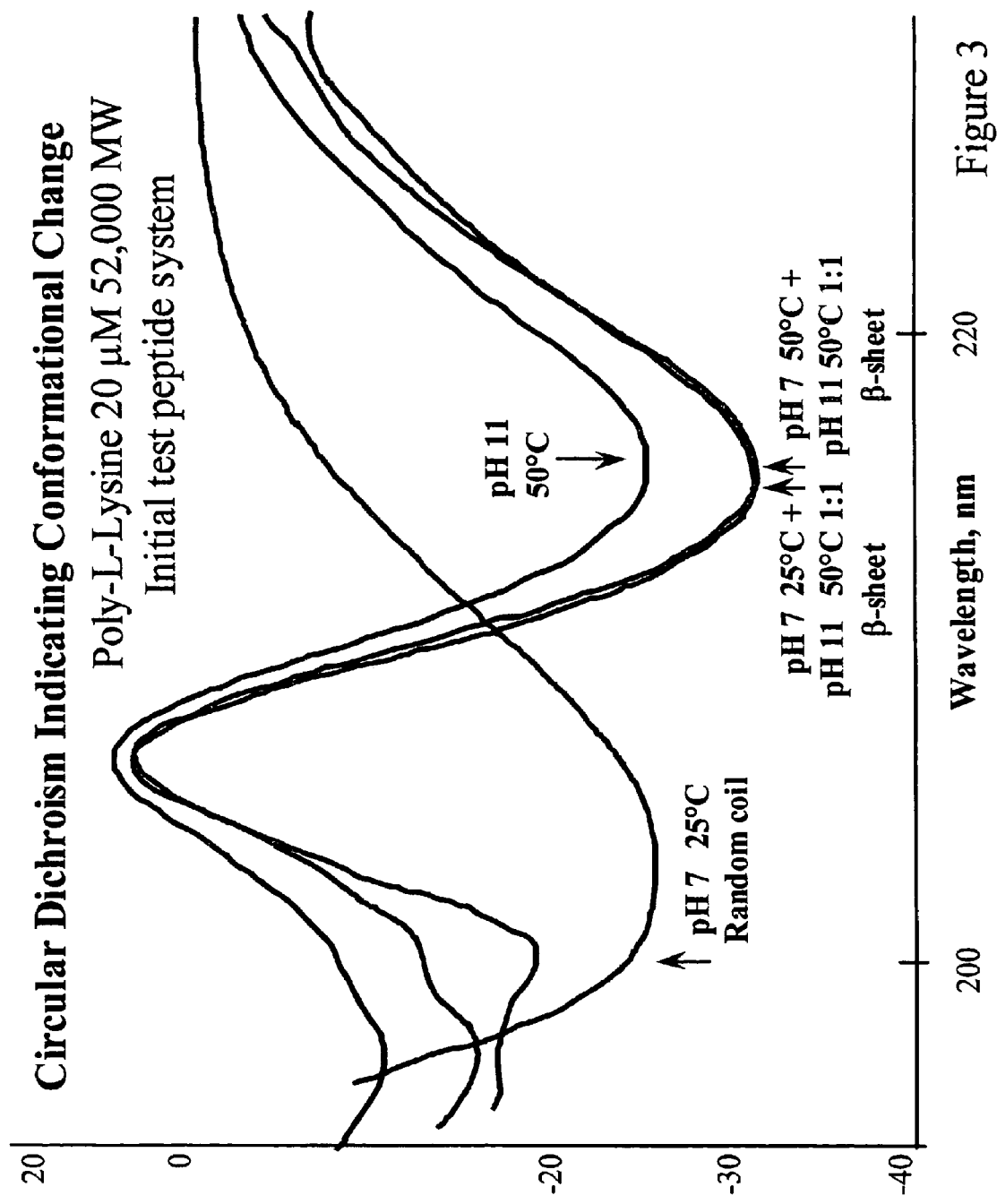
FIG. 3 illustrates a circular dichroism graph of a diagnostic analysis that was performed in accordance with the invention and that used a poly-L-lysine 20 micromolar (μM) 52,000 molecular weight (MW) as a peptide-model.

FIG. 3 depicts a CD graph of an experiment in which poly-L-lysine 20 micro Molar (μμM) 52,000 molecular weight (MW) was used as a peptide model.

As also illustrated in FIG. 3:

Sample 24, which was maintained at pH 7, 25° C., exhibited a minimum at approximately 205 nanometers (nm), indicating a random coil structure;

Sample 26 which was maintained at pH 11 (near the isoelectric point), at 50° C., resulted in a minimum at approximately 216 nanometers (nm) indicating a β-sheet structure (see FIG. 11 for exemplary CD spectra of protein conformations);

Sample 28, which was a 1:1 combination of samples maintained at pH7, 25° C. and at pH11, 50° C., resulted in a minimum at approximately 216 nanometers (nm) indicating β-sheet structure;

Sample 30, which was a 1:1 combination of samples maintained at pH 7, 50° C. and at pH 11, 50° C., resulted in a minimum at approximately 216 nanometers (nm), indicating β-sheet structure.

EXAMPLE 3

Figure 4:
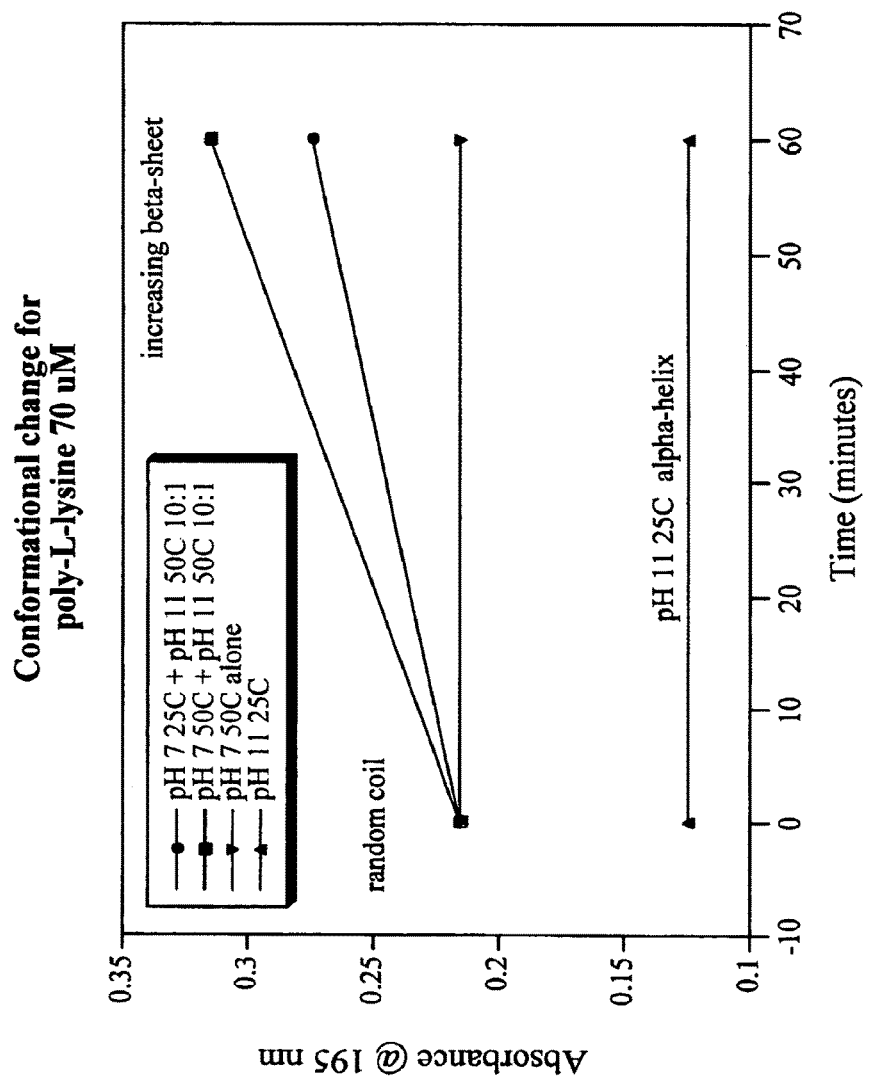
FIG. 4 illustrates an absorbance graph of a diagnostic analysis that was performed using poly-L-lysine, 70 micromolar (μM) 52,000 molecular weight (MW), as a peptide-model.
Figure 5:
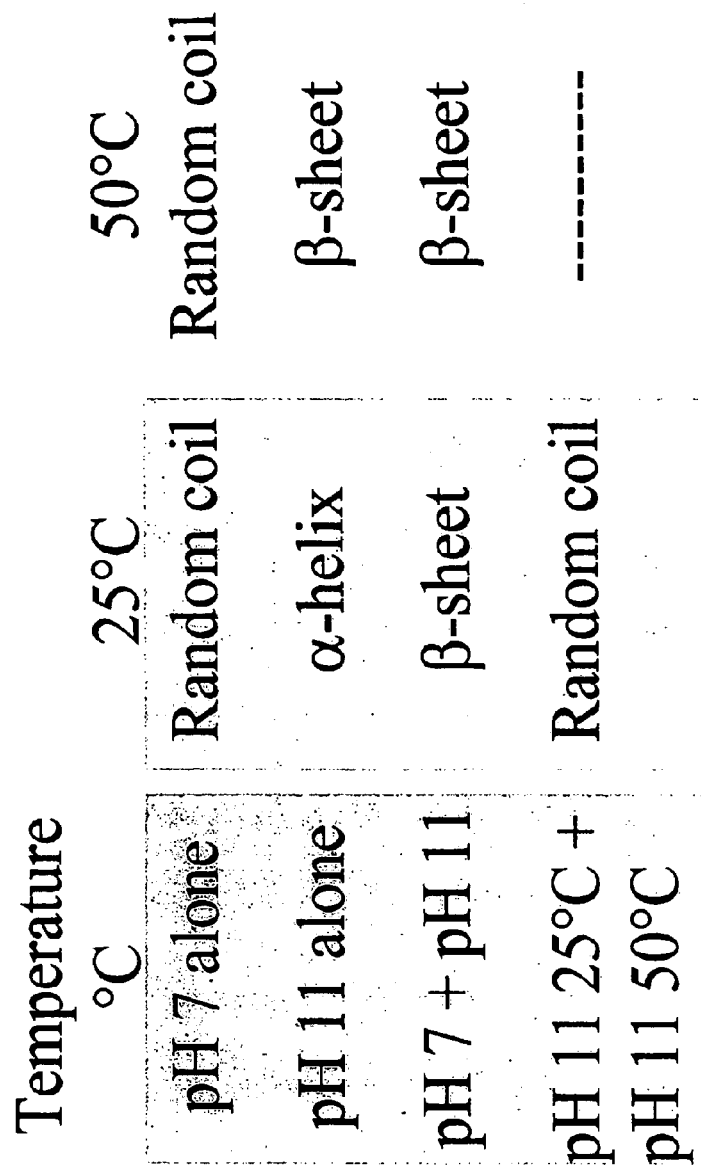
FIG. 5 illustrates the results from FIG. 3, that used a poly-L-lysine, 70 micromolar (μM) 52,000 molecular weight (MW) as a peptide model and the effect of pH and temperature on conformational change.
Figure 6:
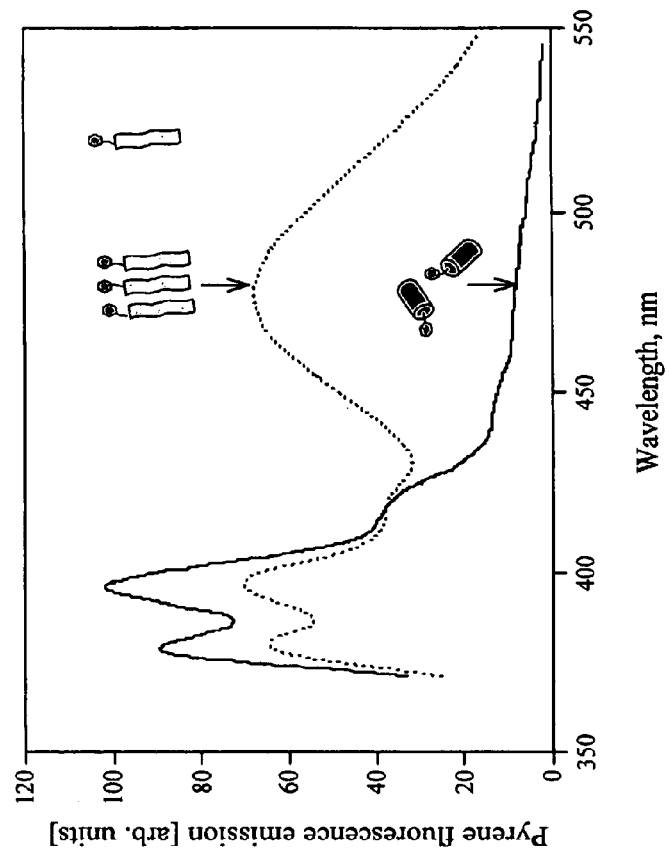
FIG. 6 illustrates a spectroscopic analysis that used pyrene as a fluorescent probe in proximal and distal locations in an alpha helical bundle structure that underwent conformational change.
Figure 7:
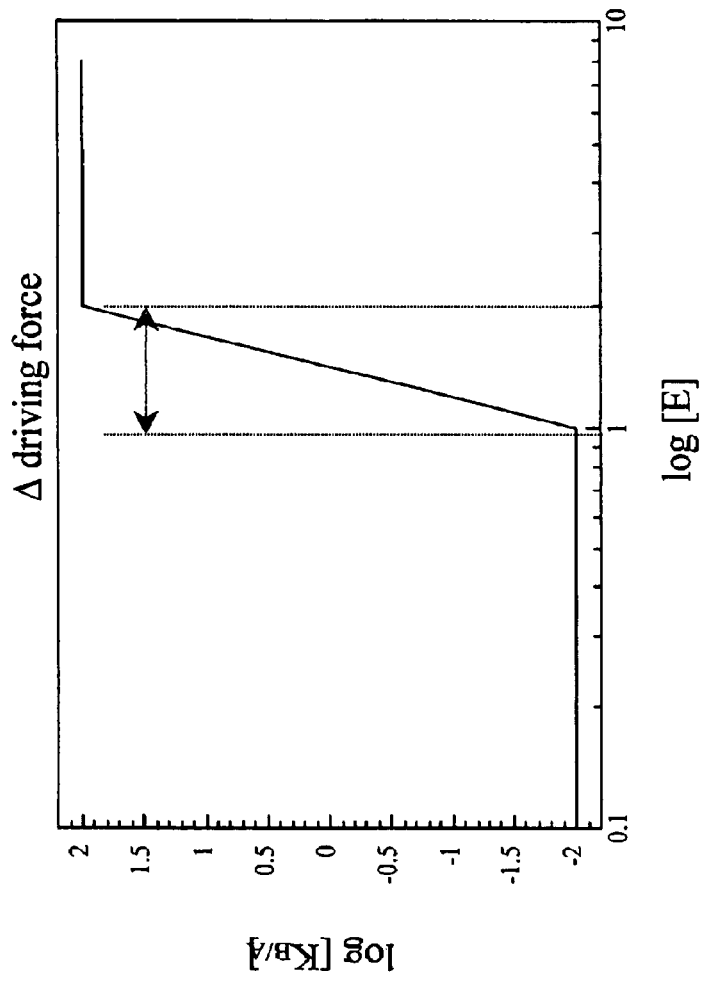
FIG. 7 illustrates energy changes associated with conformational changes in proteinaceous material or prions.
Figure 8:
FIG. 8 illustrates the alpha-helix and loop structure of PrP.
Figure 9:
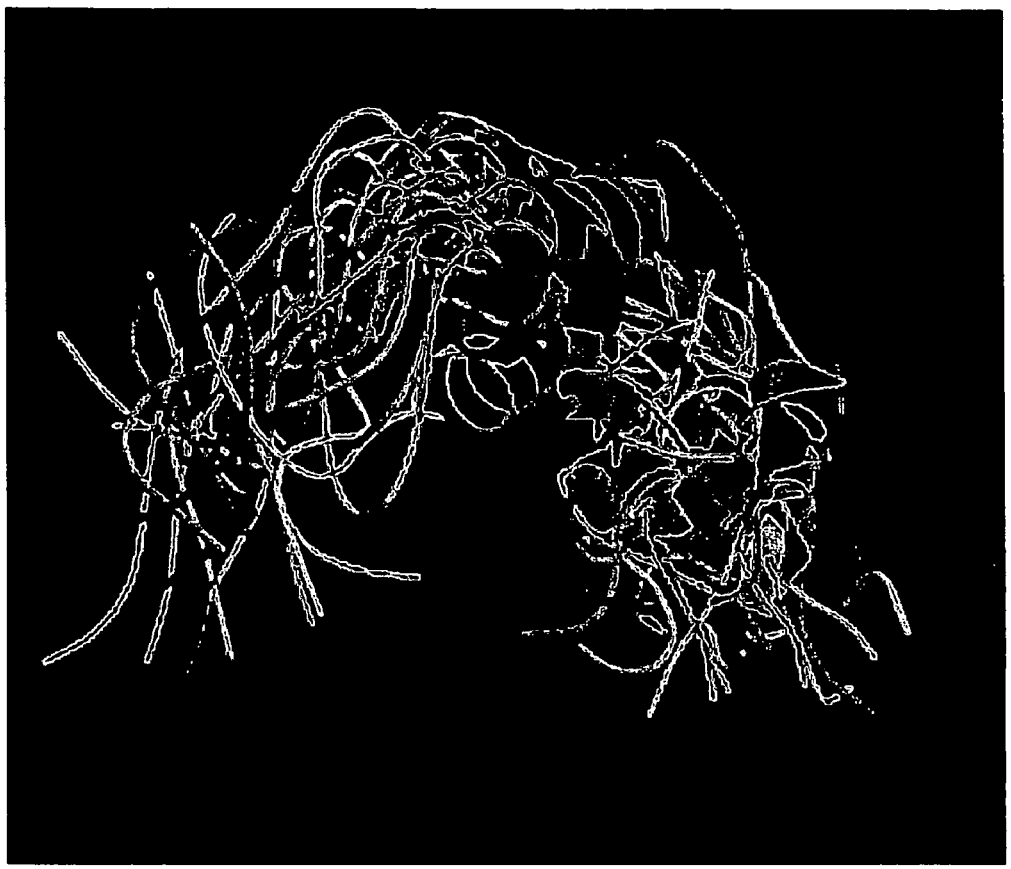
FIG. 9 illustrates the predominantly beta-sheet secondary structure of PrP$^{Sc}$.

FIG. 4 illustrates general CD results of experiments that were conducted: (1) using poly-L-lysine; and (2) at varying temperatures and pH, to observe the effect of random coil to beta-sheet conformational changes under varying environmental conditions. The results indicate that both temperature and pH play an important role in the transition. The results also indicate that the addition of a relatively small amount of β-sheet peptide to a random coil sample can result in a shift towards a β-rich conformation and that such changes can be accelerated depending on the temperature and pH environment of the samples.

More specifically, FIG. 4 illustrates an absorbance graph generated using a poly-L-lysine of 52,000 molecular weight (MW) at 70 micromolar (μM) as a peptide probe in accordance with the experimental technique described in Examples 1-3. FIG. 4 illustrates that:

Sample 32 (pH 11, 25° C.) evidenced a plateau at approximately 0.12, indicating a predominantly α-helical structure;

Sample 34 (maintained at pH 7, 50° C.) evidenced a plateau at approximately 0.22, which indicated a predominantly random coil structure;

Sample 36 (a 10:1 combination of samples maintained at pH 7, 50° C. and at pH 11, 50° C.) resulted in a steeper incline from approximately 0.22 to 0.33, indicating an accelerated transition from random coil to β-sheet structure;

Sample 38 (a 10:1 combination of samples maintained at pH 7, 25° C. and at pH 11, 50° C.) resulted in a gradual incline from approximately 0.22 to 0.26, indicating a transition from random coil to β-sheet structure.

The observations based on all of the experiments described above show that the addition of a relatively small amount of β-sheet peptide to random coil sample can result in a shift towards a beta-rich conformation and that such changes can be accelerated depending on the temperature and pH environment of the samples.

EXAMPLE 4

Figure 15:
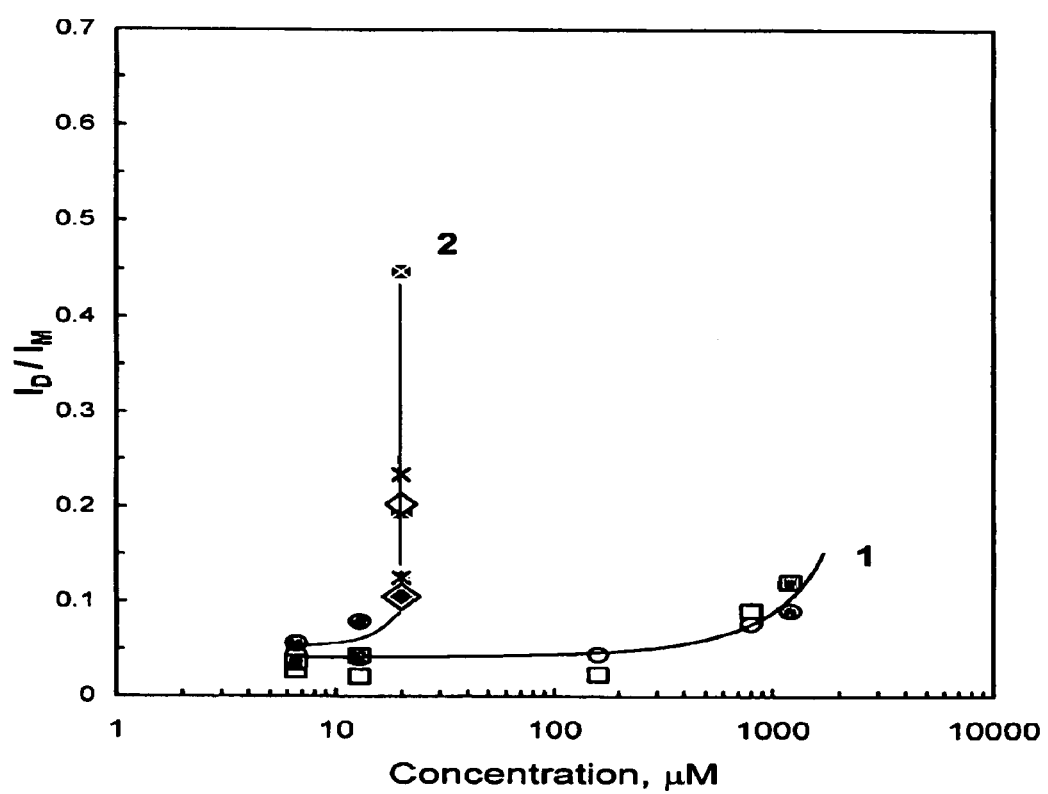
FIG. 15 illustrates the ratio of excimer formation (($I_D$) to monomer formation ($I_M$) in a diagnostic analysis that used a palindromic 33_mer probe of sequence shown in FIG. 10 under various conditions. We expect to see minimum solubility of a protein when the conditions are near its isoelectric point and that is what we observed where conditions (2) approach the isoelectric point of the 33_mer peptide—it aggregates with itself since it has dramatically reduced solubility under these conditions as compared to (1) In this example, electrostatic interactions (pI=10) trigger self-association under extremely low concentrations (10 μM) at the isoelectric point of the peptide. The following legend applies to FIG. 15.

The experiment that led to the results illustrated in FIG. 15 involved use of the 33_mer target peptide (SEQ ID NO:1 and 29)

```
VVAGAAAAGAVHKINTKPKLKHVAGAAAAGAVV  (murine)

VVAGAAAAGAMHKMNTKPKMKHMAGAAAAGAVV  (human)
``` alone, and probing peptide association through the observation of excimer formation. The 33_mer target peptide (SEQ ID NO:1 or 29) used was a murine amino acid sequence which differed from a corresponding human sequence in the substitution of methionine for valine and leucine at positions _M11V_, M14L_, M20L_, and M23V_, as illustrated in FIG. 10B. We compared the results we observed using CD (in which peptides were unlabeled) and spectrofluorometric studies (using pyrene-labeled peptides). No homogenate was used. The experiment that lead to the results illustrated in FIG. 15 was a detailed study undertaken to understand what triggered the 33_mer target peptide (SEQ ID NO:1 or 29) to conformationally change from predominantly monomeric to dimeric (excimeric) and become aggregated. Conditions were found that encouraged 33_mer labeled-peptide association in the μM-range.

Conditions that screened the electrostatic interactions of the 33_mer target peptide and thereby minimized its solubility (pI=10) triggered self-association of the peptide under extremely low concentrations (10 μM). This self association is evident in the formation of dimers or excimers and the concomitant far red shift in fluorescence by virtue of the pyrene fluorophor on the ends of the peptides. As an example, Curve 1 of FIG. 15 represents the conditions of pH 6-8, KCl (100-500 μM) where the predominant peptide conformer is monomeric; while Curve 2 of FIG. 15 represents the conditions of pH 10-11, KCl (100-500 μM), where at very low concentrations of peptide, we observed strong excimer formation (aggregation of the monomers).

EXAMPLE 5

The experiment that led to the results illustrated in FIG. 16 involved use of various individual peptides, and the 33_mer probe (comprising 19_mer and 14_mer) target peptide (SEQ ID NO:1, 29, 2 or 3)

```
VVAGAAAAGAVHKLNTKPKLKHVAGAAAAGAVV  (murine)

VVAGAAAAGAMBKMNTKPKMKHMAGAAAAGAVV  (human)
```

The assay conditions were changed to observe the effect on conformation as monitored by CD. The goal was to determine what thermodynamic conditions result in one step transition from monomeric random coil to aggregated β sheet and avoid the associative 'X' state that is probably micelle formation of the peptides.

In the experiment that lead to the results illustrated in FIG. 16, a specific λ (205 nm) wavelength was used to monitor peptide association by CD to obtain detailed conformational information over a range of solvent conditions and across a range of peptide concentrations (peptide concentrations are presented in log scale and also refer to the standard diagram for CD—FIG. 11).

The associative curve ($\theta_{205}$) recovered for the target peptides showed two conformational transitions at the 50 μM and 3 mM range, respectively, moving from a coil through to 'X' state and to β-sheet.

Referring to FIG. 16, for solvent conditions above 50% (far left dashed line), the 33_mer target peptide (SEQ ID NO:1 and 29)

```
VVAGAAAAGAVHKLNTKPKLKHVAGAAAAGAVV  (murine)

VVAGAAAAGAMHKMNTKPKMKHMAGAAAAGAVV  (human)
``` transitioned from the coil state to a β-sheet state at 3 μM, while the component 19_mer or 14_mer were able to transition, but at nearly 10-fold higher peptide concentration (middle line). Under aqueous conditions, (thick line) none of the peptides were able to self associate into a β sheet structure.

The 33_mer palindromic peptide target peptide (SEQ ID NO:1 and 29) exhibited unique properties at very low concentrations (ie. 1 μM) under 50% solvent (acetonitrile or trifluoroethanol) conditions in that it avoided the "dead-end" associative state (as exhibited by the plateauing effect under aqueous conditions).

FIG. 16 shows that a variation in solvent and temperature does not significantly affect the associative behavior of target peptides and that all of the peptides follow the same curve, indicating that sequence specificity is not an important feature in this kind of molecular assembling.

EXAMPLE 6

The experiment that led to the results illustrated in FIG. 17 was conducted as follows.

One gram of scrapie infected (strain 293) hamster brain material was homogenized in liquid nitrogen in sterile phosphate buffered saline. Ten-fold serial dilutions were made into sterile PBS. The concentration of protease resistant prion protein ($PrP^{Sc}$) in the brain homogenates was determined by capillary electrophoresis antibody-capture. Brain homogenate equivalent to 10 ng of protease resistant prion protein ($PrP^{Sc}$) was mixed with 1.5 μM of 33_mer target peptide in 50% TFE (trifluoroethanol) and incubated for 1 hour at room temperature prior to excitation at 350 nm in a dual chronometer spectrofluorometer and emission from 350 to 600 nm recorded, the excitation and emission scan was repeated at 5 hours and 24 hours. The 33_mer peptide alone was used as a control.

Addition of the infectious prion protein led to the significant increase in the fluorescence of the 33-_mer target peptide, which was found to be in near β-sheet conformation by CD data under conditions of 50% Tris:50% TFE. This increase of fluorescence indicated the formation of 33_mer aggregates. The 33_mer aggregates were found to be unstable and dissociated irreversibly with time.

Following the emission of fluorescence for the complex versus the peptide over time illustrated that the complex dissociated with time, while the peptide fluorescence remained stable monitoring at two different wavelengths, 377 nm (triangle) and 475 nm (square).

EXAMPLE 7

The experiment that led to the results illustrated in FIG. 18 was conducted as follows.

One gram of scrapie infected and healthy hamster brain, sheep brain and elk brain were homogenized in liquid nitrogen in sterile phosphate buffered saline. Ten-fold serial dilutions were made into sterile PBS. The concentration of protease resistant prion protein ($PrP^{Sc}$) in the brain homogenates was determined by capillary electrophoresis antibody-capture. Brain homogenates, infected and healthy, were mixed with 0.52 µM of 33_mer target peptide in 50% TFE (trifluoroethanol):50% TRIS and incubated for 1 hour at room temperature prior to excitation at 350 nm in a dual chromometer spectrofluorometer and emission at 350 to 600 nm recorded. The 33_mer peptide alone in 50% TFE:50% TRIS was used as an additional control.

Fluorescence spectra of the target peptide [520 nM] in the presence of infected brain homogenate (graph line 1–), healthy brain homogenate (graph line 2–), and peptide alone (graph line 3–) in TRIS:TFE (1:1) solvent are shown in FIG. 18. The data are for 0.01% brain homogenate from hamster (panel A), sheep (panel B), and elk (panel C). hamster [270 pg/ml], sheep [60 pg/ml], and elk [6 pg/ml].

What is claimed is:

1. A method for detecting misfolded Aβ peptide in a sample comprising:

(a) contacting a liquid sample that comprises a liquid biological sample obtained from a subject and does not contain homogenized tissue with a peptide probe comprising an amino acid sequence corresponding to a β-sheet forming region of said Aβ peptide, wherein the peptide probe exhibits a random coil or alpha-helix conformation in solution and undergoes a transition to a β-sheet conformation upon interaction with Aβ peptide exhibiting a β-sheet conformation, wherein the amino acid sequence of the peptide probe comprises a sequence that is at least 70% identical to any one of SEQ ID NOs: 4-7, (b) permitting the peptide probe to interact with any misfolded Aβ peptide present in the sample; and (c) detecting any interaction between the peptide probe and any misfolded Aβ peptide present in the sample.

2. The method of claim 1, wherein the peptide probe is labeled with a detectable label.

3. The method of claim 1, wherein (i) both termini of the peptide probe are labeled with a fluorophore capable of forming excimers and (ii) the detecting step comprises detecting any excimers formed upon interaction between the fluorophore-labeled peptide probe and any Aβ peptide present in the sample.

4. The method of claim 1, wherein the detecting step comprises using circular dichroism to detect any interaction between the peptide probe and any Aβ peptide present in the sample.

5. The method of claim 1, further comprising, prior to the contacting step, subjecting the sample to a disaggregation step.

6. The method of claim 1, wherein the liquid sample comprises a liquid biological sample selected from the group consisting of blood, a blood fraction, plasma, serum, and spinal fluid.

7. The method of claim 1, wherein the peptide probe comprises an amino acid sequence that is at least about 90% identical to an amino acid sequence selected from the group consisting of SEQ ID NOs 4-7.

8. The method of claim 1, wherein the peptide probe consists of from 10 to 50 amino acids.

9. The method of claim 1, wherein the amino acid sequence corresponding to a β-sheet forming region of the Aβ peptide is at least about 70%, at least about 90% or 100% identical to the β-sheet forming region of the Aβ peptide.

10. The method of claim 2, wherein the detectable label is selected from (i) optically detectable moieties and (ii) radionuclides.

11. The method of claim 10, wherein the detectable label is a chromophore.

12. The method of claim 10, wherein the detectable label is selected from pyrene, tryptophan, fluorescein, rhodamine, 1-anilino-8-napthalene sulfonate (ANS), Congo Red stain and fluorescence resonance energy transfer (FRET) labels.

* * * * *